US007615570B2

(12) United States Patent
Brown et al.

(10) Patent No.: US 7,615,570 B2
(45) Date of Patent: Nov. 10, 2009

(54) ANTAGONISTS TO THE VANILLOID RECEPTOR SUBTYPE 1 (VR1) AND USES THEREOF

(75) Inventors: Brian S. Brown, Evanston, IL (US); Tammie K. Jinkerson, Kenosha, WI (US); Ryan G. Keddy, Beach Park, IL (US); Chih-Hung Lee, Vernon Hills, IL (US)

(73) Assignee: Abbott Laboratories, Abbott Park, IL (US)

( * ) Notice: Subject to any disclaimer, the term of this patent is extended or adjusted under 35 U.S.C. 154(b) by 314 days.

(21) Appl. No.: 11/294,316

(22) Filed: Dec. 5, 2005

(65) Prior Publication Data
US 2006/0148867 A1 Jul. 6, 2006

Related U.S. Application Data

(60) Provisional application No. 60/635,491, filed on Dec. 13, 2004.

(51) Int. Cl.
*A61K 31/44* (2006.01)
*C07D 417/04* (2006.01)
*C07D 275/06* (2006.01)

(52) U.S. Cl. .................. 514/373; 546/268.1; 546/268.4; 546/271.1; 548/206; 548/207; 548/212; 514/337; 514/338; 514/372

(58) Field of Classification Search .............. 546/268.1, 546/268.4, 271.1; 548/206, 207, 212; 514/336, 514/337, 338, 372, 373
See application file for complete search history.

(56) References Cited

U.S. PATENT DOCUMENTS

| 4,147,698 | A | 4/1979 | Wade et al. |
| 4,166,910 | A | 9/1979 | Wade et al. |
| 4,743,692 | A | 5/1988 | Teller et al. |

FOREIGN PATENT DOCUMENTS

| WO | 2004/108133 | 12/2004 |
| WO | 2005/009982 | 2/2005 |

OTHER PUBLICATIONS

Teller et al (1988): STN International HCAPLUS database, (Columbus, Ohio), Accession No. 1988:492994.*
Blum et al (2005): STN International HCAPLUS database, (Columbus, Ohio), Accession No. 2005:99489.*
Berge, S.M., et al., "Pharmaceutical Salts", *J. Pharmaceutical Sciences*, 66(1):1-17 (1977).
Caterina, M.J. and Julius, D., "The Vanilloid Receptor: A Molecular Gateway to the Pain Pathway", *Annu. Rev. Neurosci.*, 24:487-517 (2001).
Caterina, et al., "The capsaicin receptor: a heat-activated ion channel in the pain pathway", *Nature*, 389:816-824 (1997).
Caterina, et al., "Impaired Nociception and Pain Sensation in Mice Lacking the Capsaicin Receptor", *Science*, 288:306-313 (2000).
Collier, et al., "The Abdominal Constriction Response and Its Suppression by Analgesic Drugs in the Mouse", *Br. J. Pharmacol. Chemother.*, 32:295-310 (1968).
Davis, et al., "Vanilloid receptor-1 is essential for inflammatory thermal hyperalgesia", *Nature*, 405:183-187 (2000).
Fowler, "Intravesical Treatment of Overactive Bladder", *Urology*, 55:60-64 (2000).
Hartwig, J., et al., "Recent advances in palladium- and nickel- catalyzed chemistry provide new ways to construct C-N and C-) bonds", *Angew. Chem. Int. Ed.*, 37:2046-2067 (1998).
Kiyomori, A., et al., "An Efficient Copper-Catalyzed Coupling of Aryl Halides with Imidazoles", *Tet. Lett.*, 40:2657-2640 (1999).
Klapars, A., et al., "A General and Efficient Copper Catalyst for the Amidation of Aryl Halides and the N-Arylation of Nitrogen Heterocycles", *J. Amer. Chem. Soc.*, 123:7727-7729 (2001).
Knochel, P. and Singer, R.D., "Preparation and Reactions of Polyfunctional Organozinc Reagents in Organic Synthesis", *Chem. Rev.*, 93:2117-2188 (1993).
Kwong, F.Y., et al., "Copper-Catalyzed Coupling of Alkylamines and Aryl Iodides: An Efficient System Even in an Air Atmosphere", *Org. Lett.*, 4:581-584 (2002).
Nolano, et al., Pain, "Topical capsaicin in humans: parallel loss of epidermal nerve fibers and pain sensation", 81:135,145 (1999).
Pircio, et al., "A New Method for the Evaluation of Analgesic Activity Using Adjuvant-Induced Arthritis in the Rat", *Eur. J Pharmacol.*, vol. 31(2), pp. 207-215(1975).
Sugahara, M., et al., "A Facile Copper-Catalyzed Ullmann Condensation: N-Arylation of Heterocyclic Compounds Containing an —NHCO- Moiety", *Chem. Pharm. Bull.*, 45: 719-721 (1997).
Wolfe, J.P., et al., "Rational Development of Practical Catalysts for Aromatic Carbon-Nitrogen Bond Formation", *Acc. Chem. Res.*, 13:805-818 (1998).
Wolfe, J.P., et al., "Simple, Efficient Catalyst System for the Palladium-Catalyzed Amination of Aryl Chlorides, Bromides, and Triflates", *J. Org. Chem.*, 65:1158-1174 (2000).
Yang, B.H., et al., "Palladium-catalyzed amination of aryl halides and sulfonates", *J. Organomet, Chem.*, 576:125-146 (1999).

\* cited by examiner

*Primary Examiner*—Golam M Shameem
(74) *Attorney, Agent, or Firm*—Sonali S. Srivastava

(57) ABSTRACT

Compounds having formula (I)

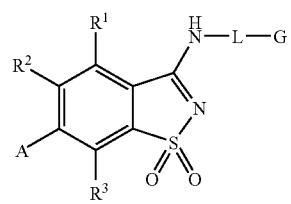

or a pharmaceutically acceptable salt, prodrug, or salt of a prodrug thereof, wherein L, A, G, $R^1$, $R^2$ and $R^3$ are as defined herein. These compounds are particularly useful in the treatment of pain, inflammatory hyperalgesia, and urinary dysfunctions, such as bladder overactivity and urinary incontinence.

19 Claims, No Drawings

ANTAGONISTS TO THE VANILLOID RECEPTOR SUBTYPE 1 (VR1) AND USES THEREOF

This application claims priority to U.S. Provisional Application Ser. No. 60/635,491 filed on Dec. 13, 2004.

TECHNICAL BACKGROUND

The present invention relates to compounds of formula (I) useful for treating disorders caused by or exacerbated by vanilloid receptor activity and pharmaceutical compositions containing compounds of formula (I). The compounds of the present invention are useful in treating pain, inflammatory hyperalgesia, and urinary dysfunctions, such as bladder overactivity and urinary incontinence.

BACKGROUND OF THE INVENTION

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as VR1. The intradermal administration of capsaicin is characterized by an initial burning or hot sensation followed by a prolonged period of analgesia. The analgesic component of VR1 receptor activation is thought to be mediated by a capsaicin-induced desensitization of the primary sensory afferent terminal. Thus, the long lasting anti-nociceptive effects of capsaicin have prompted the clinical use of capsaicin analogs as analgesic agents (Nolano et al., *Pain*, Vol 81, pages 135-145, 1999). Further, capsazepine, a capsaicin receptor antagonist can reduce inflammation-induced hyperalgesia in animal models. VR1 receptors are also localized on sensory afferents, which innervate the bladder. Capsaicin or resiniferatoxin has been shown to ameliorate incontinence symptoms upon injection into the bladder (Fowler, *Urology*, Vol. 55, pages 60-64, 2000).

The VR1 receptor has been called a "polymodal detector" of noxious stimuli since it can be activated in several ways. The receptor channel is activated by capsaicin and other vanilloids and thus is classified as a ligand-gated ion channel. VR1 receptor activation by capsaicin can be blocked by the competitive VR1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat (Caterina et al., *Nature*, Vol 389, pages 816-824).

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the VR1 receptor (VR1(−/−)). Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The VR1(−/−) mice also did not show reduced sensitivity to nerve injury-induced mechanical or thermal nociception. However, the VR1 knock-out mice were insensitive to the noxious effects of intradermal capsaicin, exposure to intense heat (50-55° C.), and failed to develop thermal hyperalgesia following the intradermal administration of carrageenan (Caterina et al., *Science*, Vol. 288, pages 306-313, 2000; Davis et al., *Nature*, Vol. 405, pages 183-187, 2000).

The compounds of the present invention are novel VR1 antagonists and have utility in treating pain, inflammatory hyperalgesia, and urinary dysfunctions, such as bladder overactivity and urinary incontinence.

SUMMARY OF THE PRESENT INVENTION

The present invention discloses novel sulfonamide compounds of formula (I), a method for inhibiting the VR1 receptor in mammals using these compounds, pharmaceutical compositions including these compounds, and methods of treating a disorder wherein the disorder is ameliorated by inhibiting vanilloid receptor subtype 1 (VR1) receptor in a host mammal in need of such treatment comprising administering a therapeutically effective amount of a compound of formula (I) as defined in claim 1 or a pharmaceutically acceptable salt thereof, and wherein the disorder is selected form the group consisting of pain, inflammatory hyperalgesia, bladder overactivity and urinary incontinence.

More particularly, the present invention is directed to compounds of formula (I)

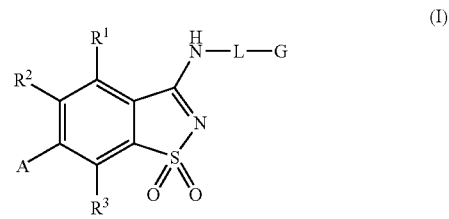

or a pharmaceutically acceptable salt, prodrug, salt of a prodrug thereof, wherein $R^1$, $R^2$ and $R^3$ are independently selected from the group consisting of hydrogen, halogen, alkyl and haloalkyl;

L is a bond or $C_{1-6}$ alkyl;

A is a ring selected from the group consisting of cycloalkyl, cycloalkenyl, heterocycle, aryl and heteroaryl; wherein each A is independently substituted with 0, 1, 2, 3, 4 or 5 substituents selected from the group consisting of alkyl, halogen, cyano, hydroxyl, alkoxy, haloalkoxy, —SH, —S(alkyl), —S(O)alkyl, —S(O)$_2$alkyl, —S(O)$_2$NH$_2$, —S(O)$_2$N(H)alkyl, —S(O)$_2$N(alkyl)$_2$, —NH$_2$, —N(H)alkyl, —N(alkyl)$_2$, —C(O)OH, —C(O)O(alkyl), —C(O)alkyl, —C(O)NH$_2$, —C(O)N(H)alkyl, —C(O)N(alkyl)$_2$, haloalkyl, cyanoalkyl, hydroxyalkyl, alkoxyalkyl, haloalkoxyalkyl, -alkylSH, -alkylS(alkyl), -alkylS(O)alkyl, -alkylS(O)$_2$alkyl, -alkylS(O)$_2$NH$_2$, -alkylS(O)$_2$N(H)alkyl, -alkylS(O)$_2$N(alkyl)$_2$, -alkylNH$_2$, -alkylN(H)alkyl, -alkylN(alkyl)$_2$, -alkylC(O)OH, -alkylC(O)O(alkyl), -alkylC(O)alkyl, -alkylC(O)NH$_2$, -alkylC(O)N(H)alkyl, and -alkylC(O)N(alkyl)$_2$;

G is a ring selected from the group consisting of cycloalkyl, cycloalkenyl, heterocycle, aryl and heteroaryl; wherein each G is independently substituted with 0, 1, 2, 3, 4 or 5 substituents selected from the group consisting of alkyl, cyano, halogen, —$OR_a$, —$OC(O)R_a$, —$OC(O)NR_aR_b$, —$SR_a$, —$S(O)R_a$, —$S(O)_2R_a$, —$S(O)_2NR_aR_b$, —$NR_aR_b$, —$C(O)OR_a$, —$C(O)R_a$, —$C(O)NR_aR_b$, $R_c$, haloalkyl, cyanoalkyl, -alkylOR$_a$, -alkylOC(O)R$_a$, -alkylOC(O)NR$_a$R$_b$, -alkylSR$_a$, -alkylS(O)R$_a$, -alkylS(O)$_2$R$_a$, -alkylS(O)$_2$NR$_a$R$_b$, -alkylNR$_a$R$_b$, -alkylC(O)OR$_a$, -alkylC(O)R$_a$, -alkylC(O)NR$_a$R$_b$, and -alkyl-R$_c$;

$R_a$, at each occurrence, is independently selected from the group consisting of hydrogen, alkyl, haloalkyl, cycloalkyl, cycloalkenyl, heterocycle, aryl, heteroaryl, arylalkyl and heteroarylalkyl; wherein the cycloalkyl, cycloalkenyl, heterocycle, aryl, heteroaryl, aryl moiety of the arylalkyl and the heteroaryl moiety of the heteroarylalkyl are independently substituted with 0, 1, 2, 3, 4 or 5 substituents selected from the group consisting of alkyl, halogen, haloalkyl, cyanoalkyl, hydroxyl, alkoxy, haloalkoxy, hydroxyalkyl, alkoxyalkyl, haloalkoxyalkyl, —SH, —S(alkyl), —S(O)alkyl, —S(O)$_2$alkyl, —S(O)$_2$NH$_2$, —S(O)$_2$N(H)alkyl, —S(O)$_2$N(alkyl)$_2$, —NH$_2$, —N(H)alkyl, —N(alkyl)$_2$, —C(O)OH, —C(O)O(alkyl) —C(O)O(aryl), —C(O)alkyl, —C(O)NH$_2$, —C(O)N(H)alkyl, and —C(O)N(alkyl)$_2$;

$R_b$, at each occurrence, is independently selected from the group consisting of hydrogen, alkyl, cycloalkyl, aryl, heterocycle, heteroaryl, arylalkyl and heteroarylalkyl; wherein each of the cycloalkyl, aryl, heterocycle, heteroaryl, aryl moiety of the arylalkyl and heteroaryl moiety of the heteroarylalkyl is independently substituted with 0, 1, 2, 3, 4 or 5 substituents selected from the group consisting of alkyl, halogen, haloalkyl, cyanoalkyl, hydroxyl, alkoxy, haloalkoxy, hydroxyalkyl, alkoxyalkyl, haloalkoxyalkyl, —SH, —S(alkyl), —S(O)alkyl, —S(O)$_2$alkyl, —S(O)$_2$NH$_2$, —S(O)$_2$N(H)alkyl, —S(O)$_2$N(alkyl)$_2$, —NH$_2$, —N(H)alkyl, —N(alkyl)$_2$, —C(O)OH, —C(O)O(aryl), —C(O)alkyl, —C(O)NH$_2$, —C(O)N(H)alkyl, and —C(O)N(alkyl)$_2$; and $R_c$, at each occurrence, is a ring independently selected from the group consisting of cycloalkyl, cycloalkenyl, heterocycle, aryl and heteroaryl; wherein each $R_c$ is independently substituted with 0, 1, 2, 3, 4 or 5 substituents selected from the group consisting of alkyl, halogen, cyano, hydroxyl, alkoxy, haloalkoxy, —SH, —S(alkyl), —S(O)alkyl, —S(O)$_2$alkyl, —S(O)$_2$NH$_2$, —S(O)$_2$N(H)alkyl, —S(O)$_2$N(alkyl)$_2$, —NH$_2$, —N(H)alkyl, —N(alkyl)$_2$, —C(O)OH, —C(O)O(alkyl), —C(O)alkyl, —C(O)NH$_2$, —C(O)N(H)alkyl, —C(O)N(alkyl)$_2$; haloalkyl, cyanoalkyl, hydroxyalkyl, alkoxyalkyl, haloalkoxyalkyl, -alkylSH, -alkylS(alkyl), -alkylS(O)alkyl, -alkylS(O)$_2$alkyl, -alkylS(O)$_2$NH$_2$, -alkylS(O)$_2$N(H)alkyl, -alkylS(O)$_2$N(alkyl)$_2$, -alkylNH$_2$, -alkylN(H)alkyl, -alkylN(alkyl)$_2$, -alkylC(O)OH, -alkylC(O)O(alkyl), -alkylC(O)alkyl, -alkylC(O)NH$_2$, -alkylC(O)N(H)alkyl, and -alkylC(O)N(alkyl)$_2$.

DETAILED DESCRIPTION OF THE PRESENT INVENTION (1) Compounds of the Invention

The present invention relates to compounds having formula (I) as described above.

The invention also includes compounds having the formula (I) wherein A is aryl, L is a bond or a $C_{1-6}$ alkyl, and G is cycloalkyl. The invention also includes compounds having the formula (I) wherein A is aryl, L is a $C_{1-6}$ alkyl and G is cycloalkenyl.

In another embodiment, the invention includes compounds having the formula (I) wherein A is aryl, L is a bond or a $C_{1-6}$ alkyl and G is aryl. In yet another embodiment, the invention includes compounds having the formula (I) wherein A is aryl, L is a bond or a $C_{1-6}$ alkyl and G is heteroaryl. In another embodiment, the invention includes compounds having the formula (I) wherein A is aryl, L is a bond or a $C_{1-6}$ alkyl and G is heterocycle.

In another embodiment, the invention includes compounds having the formula (I) wherein A is cycloalkyl, L is a bond or a $C_{1-6}$ alkyl and G is cycloalkyl. In yet another embodiment, the invention includes compounds having the formula (I) wherein A is cycloalkyl, L is a bond or a $C_{1-6}$ alkyl and G is cycloalkenyl.

In another embodiment, the invention includes compounds having the formula (I) in which A is cycloalkyl, L is a bond or a $C_{1-6}$ alkyl and G is aryl. In yet another embodiment, the invention includes compounds having the formula (I) wherein A is cycloalkyl, L is a bond or a $C_{1-6}$ alkyl and G is heteroaryl. In yet another embodiment, the invention includes compounds having the formula (I) in which A is cycloalkyl, L is a bond or a $C_{1-6}$ alkyl and G is heterocycle.

In another embodiment, the invention includes compounds having the formula (I) wherein A is cycloalkenyl, L is a bond or a $C_{1-6}$ alkyl and G is cycloalkyl. In another embodiment, the invention includes compounds having the formula (I) wherein A is cycloalkenyl, L is a bond or a $C_{1-6}$ alkyl and G is cycloalkenyl.

In another embodiment, the invention includes compounds having the formula (I) wherein A is cycloalkenyl, L is a bond or a $C_{1-6}$ alkyl and G is aryl. In another embodiment, the invention includes compounds having the formula (I) in which A is cycloalkenyl, L is a bond or a $C_{1-6}$ alkyl and G is heteroaryl. In another embodiment, the invention includes compounds having the formula (I) in which A is cycloalkenyl, L is a bond or a $C_{1-6}$ alkyl and G is heterocycle.

In another embodiment, the invention includes compounds having the formula (I) wherein A is heterocycle, L is a bond or a $C_{1-6}$ alkyl and G is cycloalkyl. In another embodiment, the invention includes compounds having the formula (I) wherein A is heterocycle, L is a bond or a $C_{1-6}$ alkyl and G is cycloalkenyl. In yet another embodiment, the invention includes compounds having the formula (I) wherein A is heterocycle, L is a bond or a $C_{1-6}$ alkyl, and G is aryl. In another embodiment, the invention includes compounds having the formula (I) wherein A is heterocycle, L is a bond or a $C_{1-6}$ alkyl and G is heteroaryl. In yet another embodiment, the invention includes compounds having the formula (I) wherein A is heterocycle, L is a bond or a $C_{1-6}$ alkyl and G is heterocycle.

In another embodiment, the present invention includes compounds having formula (I) in which A is heteroaryl, L is a bond or a $C_{1-6}$ alkyl, and G is cycloalkyl. In another embodiment, the present invention includes compounds having formula (I) in which A is heteroaryl, L is a bond or a $C_{1-6}$ alkyl, and G is cycloalkenyl.

In a preferred embodiment, the present invention includes compounds having formula (I) in which A is heteroaryl, L is a bond, and G is aryl. In a most preferred embodiment, A is pyridyl and G is phenyl.

In yet another preferred embodiment, the present invention includes compounds having formula (I) in which A is heteroaryl, L is a bond, and G is heterocycle, most preferably benzodioxolyl.

In another preferred embodiment, the present invention includes compounds having formula (I) in which A is heteroaryl, L is a bond, and G is heteroaryl, most preferably pyridyl. In another preferred embodiment, the present invention includes compounds having formula (I) in which A is heteroaryl, L is a $C_{1-6}$ alkyl, and G is heteroaryl.

In another preferred embodiment, the present invention includes compounds having formula (I) in which A is heteroaryl, L is a $C_{1-6}$ alky, and G is aryl, preferably G is phenyl.

In another most preferred embodiment, A is pyrimidinyl, L is a bond, and G is aryl, preferably phenyl.

In another preferred embodiment, the present invention includes compounds having formula (I) in which A is heteroaryl, L is a $C_{1-6}$ alky, and G is heterocycle. Another embodiment of the present invention includes pharmaceutical compositions comprising therapeutically effective amounts of the compounds of formula (I) of the present invention, or their pharmaceutically acceptable salts.

Another embodiment of the present invention comprises a method of treating a disorder which is ameliorated by inhibiting vanilloid receptor subtype 1 (VR1) in a host mammal, that is in need of such treatment, administering a therapeutically effective amount of a compound of formula (I) or a pharmaceutically acceptable salt thereof It is understood that the present invention includes disorders selected from the group consisting of pain, inflammatory hyperalgesia, bladder overactivity and urinary incontinence.

(2) Definitions

As used throughout this specification and the appended claims, the following terms have the following meanings.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "$C_{1-6}$ alkyl" as used herein, refers to a straight or branched chain hydrocarbon containing from 1 to 6 carbon atoms. Representative examples of alkyl include, but are not limited to, methyl, ethyl, n-propyl, iso-propyl, n-butyl, sec-butyl, isobutyl, tert-butyl, n-pentyl, isopentyl, neopentyl and n-hexyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "aryl" as used herein, means a phenyl group, or a bicyclic or a tricyclic hydrocarbon fused ring system containing zero heteroatom wherein one or more of the fused rings is a phenyl group. Bicyclic hydrocarbon fused ring systems are exemplified by a phenyl group fused to a monocyclic cycloalkyl group, as defined herein, a monocyclic cycloalkenyl group, as defined herein, or another phenyl group. Tricyclic hydrocarbon fused ring systems are exemplified by the bicyclic fused hydrocarbon ring system as defined hereinabove, fused to a monocyclic cycloalkyl group, as defined herein, a monocyclic cycloalkenyl group, as defined herein, or another phenyl group. The aryl groups of the present invention are appended to the parent moiety through any substitutable atoms in the group. The aryl groups of the present invention can be unsubstituted or substituted. Representative examples of aryl include, but are not limited to, anthracenyl, azulenyl, fluorenyl, 2,3-dihydro-1H-inden-1-yl, 2,3-dihydro-1H-inden4-yl, inden-1-yl, inden-4-yl, naphthyl, phenyl, 5,6,7,8-tetrahydronaphthalen-1-yl, 1,2,3,4-tetrahydronaphthalen-2-yl and tetrahydronaphthyl.

The term "arylalkyl" as used herein, refers to an aryl group, as used herein, appended to the parent moiety through an alkyl group as defined herein.

The term "cyano" as used herein, refers to —CN.

The term "cyanoalkyl" as used herein, refers to an alkyl group as defined herein, in which one or two hydrogen atoms are replaced by cyano. Representative examples of cyanoalkyl include, but are not limited to, 1-methyl-1-cyanoethyl and cyanoethyl.

The term "cycloalkyl" or "cycloalkane" as used herein, refers to a saturated monocyclic hydrocarbon ring system having three to eight carbon atoms and zero heteroatom. Examples of monocyclic ring systems include cyclopropyl, cyclobutyl, cyclopentyl, cyclohexyl, cycloheptyl, and cyclooctyl. The term "cycloalkyl" of the present invention also include a bicyclic fused ring system wherein the cycloalkyl ring is fused to another monocyclic cycloalkyl group, as defined herein. The cycloalkyl groups of the present invention can be unsubstituted or substituted, and are connected to the parent molecular moiety through any substitutable carbon atom of the group.

The term "cycloalkenyl" or "cycloalkene" as used herein, refers to a non-aromatic, partially unsaturated, monocyclic hydrocarbon ring system, having 4, 5, 6, 7 or 8 carbon atoms and zero heteroatom. The 4-membered ring systems have one double bond, the 5- or 6-membered ring systems have one or two double bonds, and the 7- or 8-membered ring systems have one, two or three double bonds. Representative examples of cycloalkenyl groups include, but not limited to, cyclobutenyl, cyclopentenyl, cyclohexenyl, cycloheptenyl and cyclooctenyl. The term "cycloalkenyl" of the present invention also include a bicyclic fused ring system wherein the monocyclic cycloalkenyl ring is fused to a monocyclic cycloalkyl group, as defined herein, or another monocyclic cycloalkenyl group, as defined herein. Representative examples of the bicyclic cycloalkenyl groups include, but not limited to, 4,5,6,7-tetrahydro-3aH-indene, octahydronaphthalenyl and 1,6-dihydro-pentalene. The cycloalkenyl groups of the present invention can be unsubstituted or substituted, and are attached to the parent molecular moiety through any substitutable carbon atom of the group.

The term "halo" or "halogen" as used herein, means —Cl, —Br, —I or —F.

The term "haloalkoxy" as used herein, refers to an alkoxy group, as defined herein, in which one, two, three or four hydrogen atoms are replaced by halogen. Representative examples of haloalkoxy include, but are not limited to, chloromethoxy, 2-fluoroethoxy, trifluoromethoxy, 2-chloro-3-fluoropentyloxy, and pentafluoroethoxy.

The term "haloalkyl" as used herein, refers to an alkyl group, as defined herein, in which one, two, three or four hydrogen atoms are replaced by halogen. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic" as used herein, refers to a monocyclic or bicyclic, non-aromatic, saturated or partially unsaturated ring system. Monocyclic ring systems are exemplified by a 4-membered ring containing one heteroatom independently selected from oxygen, nitrogen and sulfur; or a 5-, 6-, 7-, or 8-membered ring containing one, two or three heteroatoms wherein the heteroatoms are independently selected from nitrogen, oxygen and sulfur. The 5-membered ring has 0 or 1 double bond. The 6-memebered ring has 0, 1 or 2 double bonds. The 7- or 8-membered ring has 0, 1, 2 or 3 double bonds. Representative examples of monocyclic ring systems include, but are not limited to, azetidinyl, azepanyl, azepinyl, diazepinyl, dioxolanyl, dioxanyl, dithianyl, imidazolinyl, imidazolidinyl, isothiazolinyl, isothiazolidinyl, isoxazolinyl, isoxazolidinyl, morpholinyl, 3-oxo-morpholinyl, oxadiazolinyl, oxadiazolidinyl, oxazolinyl, 2-oxo-oxazolinyl, oxazolidinyl, piperazinyl, piperidyl, pyranyl, pyrazolinyl, pyrazolidinyl, pyrrolinyl, pyrrolidinyl, tetrahydrofuryl, tetrahydropyranyl, tetrahydropyridyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, 1,4-diazepanyl and trithianyl. Bicyclic ring systems are exemplified by any of the above monocyclic ring systems fused to a phenyl group, a monocyclic cycloalkenyl group, as defined herein, a monocyclic cycloalkyl group, as defined herein, or an additional monocyclic heterocycle group, as defined herein. Representative examples of bicyclic ring systems include but are not limited to, benzodioxinyl, benzodioxolyl, benzopyranyl, benzothiopyranyl, 2,3-dihydroindolyl, indolizinyl, tetrahydroisoquinolinyl, tetrahydroquinolinyl, 3-azabicyclo[3.2.0]heptyl, 3,6-diazabicyclo[3.2.0]heptyl, octahydrocyclopenta[c]pyrrolyl, hexahydro-1H-furo[3,4-c]pyrrolyl, and octahydropyrrolo[3,4-c]pyrrolyl. The monocyclic or bicyclic ring systems as defined herein may have two of the non-adjacent carbon atoms connected by a heteroatom selected from nitrogen, oxygen or sulfur, or an alkylene bridge of between one and three additional carbon atoms. Representative examples of monocyclic or bicyclic ring systems that contain such connection between two non-adjacent carbon atoms include, but not limited to, 2-azabicyclo[2.2.2]octyl, 2-oxa-5-azabicyclo[2.2.2]octyl, 2,5-diazabicyclo[2.2.2]octyl, 2-azabicyclo[2.2.1]heptyl, 2-oxa-5-azabicyclo[2.2.1]heptyl, 2,5-diazabicyclo[2.2.1]heptyl, 2-azabicyclo[2.1.1]hexyl, 5-azabicyclo[2.1.1]hexyl, 3-azabicyclo[3.1.1]heptyl, 6-oxa-3-azabicyclo[3.1.1]heptyl, 8-azabicyclo[3.2.1]octyl, 8-azabicyclo[3.2.1]oct-8-yl, 3-azabicyclo[3.2.1]octyl, 1,4-diazabicyclo[3.2.2]nonyl, 1,4-diazatricyclo[4.3.1.1$^{3,8}$]undecyl, 3,10-diazabicyclo[4.3.1]decyl, or 8-oxa-3-azabicyclo[3.2.1]octyl, octahydro-1H-4,7-methanoisoindolyl, and octahydro-1H-4,7-epoxyisoindolyl. The heterocycle groups of the invention are substituted or unsubstituted, and are connected to the parent molecular moiety through any substitutable carbon or nitrogen atom in the groups. The nitrogen heteroatom may or may not be quaternized, and the nitrogen or sulfur heteroatom may or may not be oxidized. In addition, the nitrogen containing heterocyclic rings may or may not be N-protected.

The term "heteroaryl" as used herein, refers to an aromatic five- or six-membered ring where at least one atom is selected from the group consisting of N, O, and S, and the remaining atoms are carbon. The five membered rings have two double bonds, and the six membered rings have three double bonds. The term "heteroaryl" also includes bicyclic systems where a heteroaryl ring is fused to a phenyl group, a monocyclic cycloalkyl group, as defined herein, a monocyclic cycloalkenyl group, as defined herein, a monocyclic heterocycle group, as defined herein, or an additional monocyclic heteroaryl group. Representative examples of heteroaryl groups include, but not limited to, benzothienyl, benzoxazolyl, benzimidazolyl, benzoxadiazolyl, 6,7-dihydro-1,3-benzothiazolyl, furyl, imidazolyl, imidazo[1,2-a]pyridinyl, indazolyl, indolyl, isoindolyl, isoxazolyl, isoquinolinyl, isothiazolyl, naphthyridinyl, oxadiazolyl, oxazolyl, pyridoimidazolyl, pyridyl, pyridazinyl, pyrimidinyl, pyrazinyl, pyrazolyl, pyrrolyl, quinolinyl, thiazolyl, thienyl, triazolyl, thiadiazolyl, tetrazolyl, 1,2,3,4-tetrahydro-1,8-naphthyridin-2-yl, and 5,6,7,8-tetrahydroquinolin-5-yl. The heteroaryl groups of the present invention can be substituted or unsubstituted, and are connected to the parent molecular moiety through any substitutable carbon or nitrogen atom in the groups. In addition, the nitrogen heteroatom may or may not be quaternized, the nitrogen and the sulfur atoms in the group may or may not be oxidized. Also, the nitrogen containing rings may or may not be N-protected.

The term "heteroarylalkyl" as used herein, means an heteroaryl group, as defined herein, appended to the parent molecular moiety through an alkyl group, as defined herein.

The term "heteroatom" as used herein, refers to nitrogen, oxygen or sulfur atom.

The term "hydroxy" or "hydroxyl" as used herein, means an —OH group.

The term "hydroxyalkyl" as used herein, refers to an alkyl group, as defined herein, in which one or two hydrogen atoms are replaced by a hydroxyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

(3) Schemes

The compounds and processes of the present invention will be better understood in connection with the following synthetic schemes, which illustrate the methods by which the compounds of the invention may be prepared. Starting materials can be obtained from commercial sources or prepared by well-established literature methods known to those of ordinary skill in the art.

This invention is intended to encompass compounds having formula (I) when prepared by synthetic processes or by metabolic processes. Preparation of the compounds of the invention by metabolic processes includes those occurring in the human or animal body (in vivo) or processes occurring in vitro.

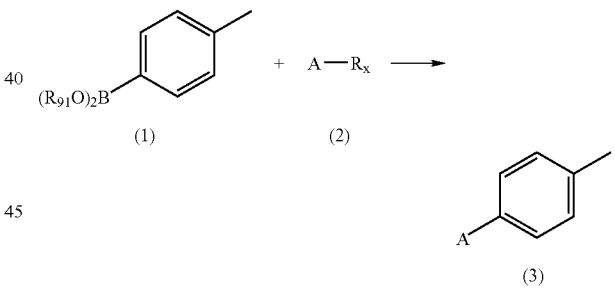

Compounds of formula (3) wherein A is as defined in formula (I) can be prepared as depicted in Scheme 1. p-Tolylboronic acid of formula (1) wherein $R_{91}$ is hydrogen, can be reacted with halides of formula (2) wherein $R_x$ is triflate, —Br, —Cl, or —I, purchased or prepared by methodologies known to those skilled in the art, a metal catalyst, a base, and optionally with a Pd ligand added. The reaction can be performed in a solvent such as, but is not limited to, tetrahydrofuran, N,N-dimethylformamide, 1,4-dioxane and the like, at a temperature from about 20° C. to about 120° C. Examples of metal catalysts include, but are not limited to, palladium diacetate, tetrakis(triphenylphosphine)palladium(0), tris(dibenzylideneacetone)dipalladium(0) ($Pd_2(dba)_3$), dichloro(di-tert-butylphosphinous acid) palladium (II) dimmer, and [1,1'-bis(diphenylphosphino)ferrocene]dichloropalladium (II) ($PdCl_2(dppf)$). Examples of bases include, but are not limited to, 0.2 M $K_3PO_4$, $CsCO_3$, CsF, KF, and $Na_2CO_3$. Examples of palladium ligands include, but are not limited to, (dicyclohexylphosphinyl)biphenyl, trifurylphosphine, tris(tert-butyl) phosphine, and triphenylphosphine. Boronic acid esters of formula (I) wherein $R_{91}$ is alkyl, can be used in place of boronic acids in the aforesaid reaction. Boronic acids can be esterified to the corresponding boronic acid esters with alcohols such as methanol or with diols such as pinacol.

Alternatively, compounds of formula (3) can be prepared from boronic acid or the corresponding esters of formula A-B(OR$_{91}$)$_2$, and the halides or triflates of toluene, using the aforesaid reaction conditions and reagents.

There are many aryl, heteroaryl, and heterocyclic boronic acids and boronic acid esters that are available commercially or that can be prepared as described in the scientific literature of synthetic organic chemistry.

Scheme 2

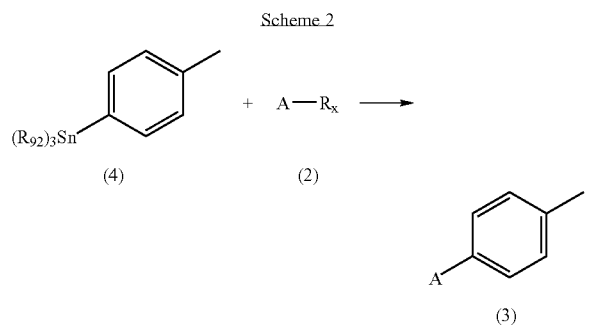

Alternatively, using Stille coupling, compounds of formula (3) wherein A is as defined in formula (I), can be prepared from compounds of formula (2) wherein $R_x$ is triflate, Cl, Br, or I, by treatment with stannanes of formula (4) wherein $R_{92}$ is alkyl, a palladium source such as tris(dibenzylidineacetone)dipalladium(0) or palladium diacetate, and a ligand such as tri(2-furyl)phosphine or triphenyl arsine in a solvent, for example in N,N-dimethylformaide at a temperature from about 25° C. to about 150° C.

Conversely, compounds of formula (3) can also be prepared from organotin reagents of formula A-Sn(R$_{92}$)$_3$ wherein $R_{92}$ is alkyl and A is as defined in formula (I) and p-triflate-toluene, p-chloro-toluene, p-bromo-toluene, orp-iodo-toluene using the reaction conditions and reagents as described in the aforesaid reaction.

While many organotin reagents for the Stille coupling are commercially available or described in the literature, new organotin reagents can be prepared from arylhalides, aryltriflates, heteroarylhalides, heteroaryltriflates by reaction with distannanes like (Me$_3$Sn)$_2$ (hexamethyl distannane) in the presence of a palladium source like tetrakis(triphenylphosphine)palladium(0). Such methods are described, for instance, in Krische, et. al., *Helvetica Chimica Acta* Vol. 81(11):1909-1920 (1998), and in Benaglia, et al., *Tetrahedron Letters* Vol. 38 pages 4737-4740 (1997).

Scheme 3

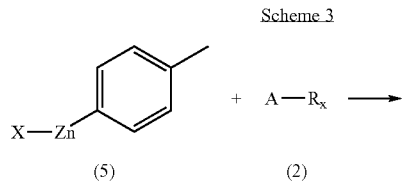

-continued

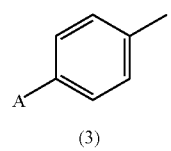

Alternatively, compounds of formula (3) wherein A is as defined in formula (I), can be prepared according to the so called Negishi coupling by reaction of a compound of formula (5) wherein X is a Cl, Br or I with a compound of formula (2) wherein $R_x$ is Cl, Br, I or triflate, in the presence of a catalyst. The catalyst may be selected from those typically employed for the reaction (for example, tetrakis(triphenylphosphine)palladium(0), tetrakis(triphenylphosphine)nickel, dichlorobis(triphenylphosphine)palladium, dichlorobis(triphenylphosphine)palladium/n-butyl lithium, dichlorobis(1,1-bis(diphenylphosphino)ferrocene)palladium and dichlorobis(1,4-bis(diphenylphosphino)butane)palladium). Suitable solvents include tetrahydrofuran, diethylether and dimethoxyethane. The reaction is typically carried out at a temperature from about 20° C. to about 160° C., usually 20° C. to 130° C. for 10 minutes to about 5 days, usually 30 minutes to about 15 hours. Alternatively, one skilled in the art will appreciate that the reactive groups of the reagents can be reversed. Thus one skilled in the art will appreciate that R, in the aforesaid reaction can be the zinc halide coupled to p-halotoluene orp-triflate tolune. (Knochel, P. and Singer, R. D. *Chem. Rev.*, Vol. 93, pages 2117-2188, 1993), Compounds of formula (3) wherein A is a nitrogen-containing heteroaryl or heterocycle ring linked to the bicyclic core group through a nitrogen can be prepared by heating p-chloro-toluene, p-bromo-toluene, p-iodo-toluene orp-triflate toluene, with a compound of formula H-A wherein H is a hydrogen on a nitrogen atom, with a base such as, but not limited to, sodium t-butoxide or cesium carbonate, in the presence of a metal catalyst such as, but not limited to copper metal or CuI, palladium diacetate, and also optionally with a ligand such as, but not limited to, 2,2'-bis(diphenylphosphino)-1,1'-binaphthalene (BINAP), tri-tertbutylphosphine in a solvent such as dioxane, toluene, N,N-dimethylformamide (DMF), N,N-dimethylacetamide, N-methylpyrrolidinone (NMP) or pyridine. References that describe these methodologies may be found in the following references: J. Hartwig et al., *Angew. Chem. Int. Ed.* Vol. 37 pages 2046-2067 (1998); J. P. Wolfe et al., *Acc. Chem. Res.*, Vol. 13 pages 805-818 (1998); M. Sugahara et al., *Chem. Pharm. Bull.*, Vol. 45 pages 719-721 (1997); J. P. Wolfe et al., *J. Org. Chem.*, Vol. 65 pages 1158-1174, (2000); F. Y. Kwong et al., *Org. Lett.*, Vol. 4 pages 581-584, (2002); A. Klapars et al., *J. Amer. Chem. Soc.*, Vol. 123 pages 7727-7729 (2001); B. H. Yang et al., *J. Organomet. Chem.*, Vol. 576 pages 125-146 (1999); and A. Kiyomori et al., *Tet. Lett.*, Vol. 40 pages 2657-2640 (1999).

Scheme 4

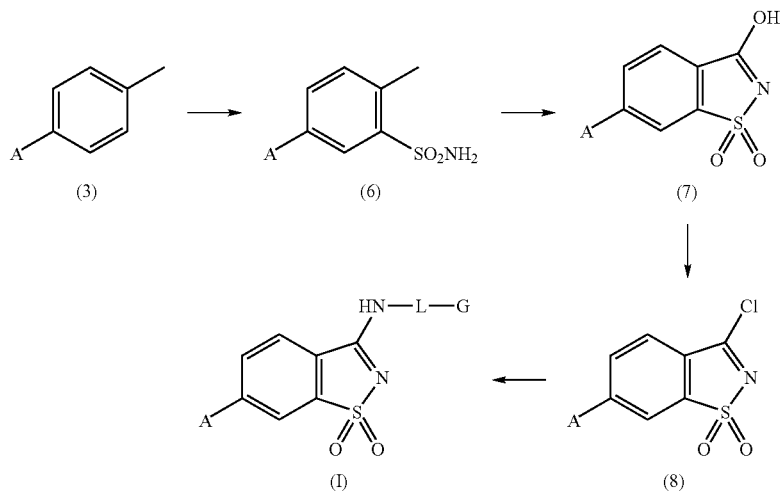

Compounds of formula (I) can be prepared from compounds of formula (3) as shown in Scheme 4. Compounds of formula (3) can be converted to sulfonamides formula (6) by (a) treating with chlorosulfonic acid, and (b) treating the product of step (a) with aqueous ammonium hydroxide. Step (a) can be performed at a temperature from about 0° C. to about 130° C. for a period of about 5 minutes to about 3 hours. Step (b) is generally carried out in a solvent such as, but not limited to, diethyl ether and the like, at a temperature from about 0° C. to about room temperature.

Sulfonamides of formula (6) can be oxidized to carboxylic acids by reacting with an oxidizing agent such as, but not limited to, permanganates such as potassium permanganate, nitric acid and acid dichromates, followed by spontaneous cyclization to provide compounds of formula (7). In general, compounds of formula (7) can be obtained by reacting sulfonamides of formula (6) with potassium permanganate in the presence of a base such as, but not limited to, aqueous sodium hydroxide, at a temperature from about 60° C. to about 100° C.

Compounds of formula (7) can be converted to compounds of formula (8) by reacting with neat phosphorusoxychloride at a temperature from about 70° C. to about 100° C., for a period of about 30 minutes to about 5 hours.

Compounds of formula (I) can be obtained from compounds of formula (8) by treatment with amines of formula G-L-NH$_2$, in the presence of a base such as, but not limited to, tertiary amines (for example, triethylamine, diisopropylethylamine, N-methylmorpholine and the like) or alkali metal carbonates (for example sodium carbonates and the like) or bicarbonates (for example, sodium bicarbonate), and in a solvent such as, but not limited to, dichloromethane, acetone, tetrahydrofuran, 1,4-dioxane, N,N-dimethylformamide, and mixture thereof The reaction is generally conducted at a temperature from about room temperature to about 100° C., for a period of about 1 hour to about 48 hours.

It is understood that the schemes described herein are for illustrative purposes and that routine experimentation, including appropriate manipulation of the sequence of the synthetic route, protection of any chemical functionality that are not compatible with the reaction conditions and deprotection are included in the scope of the invention.

(4) Examples

It is understood that the following Examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

Example 1

N-(4-tert-butylphenyl)-6-(3-chloropyridin-2-yl)-1,2-benzisothiazol-3-amine 1,1-dioxide Example 1A 3-chloro-2-(4-methylphenyl)pyridine A solution of 2,3-dichloropyridine (0.9663 g, 6.5 mmol), p-tolylboronic acid (0.8569 g, 6.3 mmol) and tetrakis(triphenylphosphine)palladium(0) (0.3618 g, 0.31 mmol) in 0.5 M Na$_2$CO$_3$ (25 mL) and acetonitrile (25 mL) was flushed with N$_2$, sealed and heated at 85° C. for 16 hours. The reaction mixture was cooled to room temperature and the volume reduced by half under vacuum. The concentrate was extracted with dichloromethane (3×20 mL), dried (MgSO$_4$) and condensed to yellow-green oil. The residue was purified by column chromatography, eluted with hexanes:ethyl acetate:dichloromethane (7:2:1)) to provide the title compound as a yellow-orange oil. MS (ESI$^+$) m/z 203 (M+H)$^+$; $^1$H NMR (DMSO-d$_6$) δ 2.38 (s, 3H), 7.30 (d, J 8.2, 2H), 7.42 (d, J 8.2, 1H), 7.59 (d, J 8.2, 2H), 8.03 (d, J 8.1, 1H), 8.62 (d, J 6.1, 1H); Anal. Calc'd for C$_{12}$H$_{10}$ClN.0.1H$_2$O: C, 70.15; H, 5.00; N, 6.82. Found: C, 70.06; H, 4.67; N, 6.67.

Example 1B

6-(3-chloropyridin-2-yl)-1,2-benzisothiazol-3-ol 1,1-dioxide

Chlorosulfonic acid (3.0 mL, 45.1 mmol) was added dropwise over 20 minutes to the product of Example 1A (2.3 g, 11.3 mmol) at about 0° C. The reaction mixture was then heated at 115° C. for 1 hour. The reaction mixture was cooled to 0° C., and treated with ice/ice water. The resulting black oily residue was extracted with dichloromethane (2×30 mL) and the isolated organic extracts were concentrated. The residue was taken into 30 mL of ether: aqueous $NH_4OH$ (1:1) and stirred until gas evolution stopped, diluted with $H_2O$ (40 mL) and extracted with ethyl acetate (3×50 mL). The combined organic fractions were washed with brine (1×50 mL), dried ($MgSO_4$), filtered and condensed to a white solid, 2.08 g. This white solid was suspended in 1 M NaOH (25 mL) and heated to 80° C. Potassium permanganate (3.55 g, 22.5 mmol) was added in small portions over 40 minutes. The reaction mixture was stirred for another 20 minutes before quenching with isopropanol (25 mL) and filtered through a plug of celite. The solution was treated with concentrated HCl (10 mL) to afford 1.24 g of the title compound as a white solid (37% yield). MS (ESI$^+$) m/z 294 (M+H)$^+$; (ESI$^-$) m/z 292 (M−H)$^-$; $^1$H NMR (DMSO-d$_6$) δ 7.57 (dd, J 4.7, 8.1, 1H), 8.09 (d, J 8.5, 1H), 8.17 (m, 2H), 8.37 (s, 1H), 8.71 (dd, J 1.4, 4.4, 1H); Anal. Calc'd for $C_{12}H_7ClN_2O_3S$: C, 48.91; H, 2.39; N, 9.51. Found: C, 48.87; H, 2.28; N, 9.25.

Example 1C

N-(4-tert-butylphenyl)-6-(3-chloropyridin-2-yl)-1,2-benzisothiazol-3-amine 1,1-dioxide A suspension of the product of Example 1B (0.1507 g, 0.51 mmol) in POCl$_3$ (4.0 mL, 42.9 mmol) was stirred at 90° C. for 90 minutes, cooled to room temperature and excess POCl$_3$ was removed under vacuum. The resulting residue was treated with 4-tert-butylaniline (0.1027 g, 0.69 mmol) in tetrahydrofuran (3 mL), followed by the addition of a solution of triethylamine (0.25 mL, 1.79 mmol) in tetrahydrofuran (2 mL), and stirred at room temperature for 16 hours. The reaction mixture was quenched with saturated NaHCO$_3$ (5 mL) and diluted with dichloromethane (5 mL). The isolated aqueous phase was extracted with dichloromethane (2×10 mL). The combined organic fractions were dried (MgSO$_4$), filtered and concentrated. The residue was purified by silica gel column chromatography, eluted with ethyl acetate/dichloromethane to afford the title compound. MS (ESI$^+$) m/z 426 (M+H)$^+$; (ESI$^-$) m/z 424 (M−H)$^-$; $^1$H NMR (300 MHz, DMSO-d$_6$) δ 1.32 (s, 9H), 7.55 (m, 3H), 7.79 (m, 2H), 8.16 (dd, J=8.3, 1.5 Hz, 1H), 8.22 (d, J=8.1 Hz, 1H), 8.30 (s, 1H), 8.60 (d, J=8.1 Hz, 1H), 8.71 (dd, J=4.7, 1.4 Hz, 1H), 10.94 (s, 1H).

Example 2

6-(3-chloropyridin-2-yl)-N-{4-[(trifluoromethyl)sulfonyl]phenyl}-1,2-benzisothiazol-3-amine 1,1-dioxide The title compound was prepared by reacting the product of Example 1B (0.1521 g, 0.52 mmol) with 4-aminophenyl trifluoromethyl sulphone (0.1417 g, 0.63 mmol) using the procedure as described in Example 1C. MS (ESI$^+$) m/z 454 (M−47)$^+$; (ESI$^-$) m/z 500 (M−H)$^-$; $^1$H NMR (300 MHz, DMSO-d$_6$) δ 7.58 (dd, J=8.3, 4.6 Hz, 1H), 8.18 (m, 1H), 8.28 (m, 3H), 8.39 (m, 3H), 8.65 (d, J=8.1 Hz, 1H), 8.72 (dd, J=4.6, 1.5 Hz, 1H), 11.42 (s, 1H).

Example 3

1-(4-{[6-(3-chloropyridin-2-yl)-1,1-dioxido-1,2-benzisothiazol-3-yl]amino}phenyl)ethanone The title compound was prepared by reacting the product of Example 1B (0.1574 g, 0.53 mmol) and 4'-aminoacetophenone (0.0876 g, 0.65 mmol) using the procedure as described in Example 1C. MS (ESI$^+$) m/z 412 (M+H)$^+$; (ESI$^-$) m/z 410 (M−H)$^-$; $^1$H NMR (300 MHz, CD$_3$OD) δ 2.63 (s, 3H), 7.51 (dd, J=8.1, 4.7 Hz, 1H), 8.07 (dd, J=8.1, 1.4 Hz, 1H), 8.11 (s, 4H), 8.19 (dd, J=8.0, 1.5 Hz, 1H), 8.30 (dd, 1H), 8.45 (d, J=8.1 Hz, 1H), 8.65 (dd, J=4.7, 1.4 Hz, 1H).

Example 4

N-(4-tert-butylbenzyl)-6-(3-chloropyridin-2-yl)-1,2-benzisothiazol-3-amine 1,1-dioxide The title compound was prepared by reacting the product of Example 1B (0.1507 g, 0.51 mmol) with 4-tert-butylbenzylamine (0.1070 g, 0.66 mmol) using the procedure as described in Example 1C. MS (ESI$^+$) m/z 440 (M+H)$^+$; (ESI$^-$) m/z 438 (M−H)$^-$; $^1$H NMR (300 MHz, CDCl$_3$) δ 1.33 (s, 9H), 4.79 (d, J=5.4 Hz, 2H), 6.14 (t, J=5.3 Hz, 1H), 7.32 (dd, J=8.0, 4.6 Hz, 1H), 7.37 (m, 2H), 7.44 (m, 2H), 7.57 (d, J=8.1 Hz, 1H), 7.85 (dd, J=8.1, 1.4 Hz, 1H), 8.03 (dd, J=8.1, 1.4 Hz, 1H), 8.34 (d, J=1.0 Hz, 1H), 8.62 (dd, J=4.4, 1.4 Hz, 1H).

Example 5

N-[2-(4-tert-butylphenyl)ethyl]-6-(3-chloropyridin-2-yl)-1,2-benzisothiazol-3-amine 1,1-dioxide The title compound was prepared by reacting the product of Example 1B (0.1523 g, 0.52 mmol) and 2-(4-tert-butylphenyl)ethylamine (0.1210 g, 0.68 mmol) using the procedure as described in Example 1C. MS (ESI$^+$) m/z 454 (M+H)$^+$; (ESI$^-$) m/z 452 (M−H)$^-$; $^1$H NMR (300 MHz, CDCl$_3$) δ 1.33 (s, 9H), 3.04 (t, J=7.0 Hz, 2H), 3.92 (q, J=6.6 Hz, 2H), 6.15 (s, 1H), 7.19 (m, 2H), 7.33 (dd, J=8.1, 4.7 Hz, 1H), 7.38 (m, 2H), 7.51 (d, J=7.8 Hz, 1H), 7.86 (dd, J=8.1, 1.0 Hz, 1H), 8.03 (dd, J=8.1, 1.4 Hz, 1H), 8.33 (d, J=1.4 Hz, 1H), 8.62 (dd, J=4.6, 0.8 Hz, 1H).

Example 6

N-[4-(8-azabicyclo[3.2.1]oct-8-yl)phenyl]-6-(3-chloropyridin-2-yl)-1,2-benzisothiazol-3-amine 1,1-dioxide

Example 6A

8-azabicyclo[3.2.1]octane

To a solution of tropane (19.5 g, 0.156 mol) in 1,2-dichloroethane (500 mL) at 0° C. was added 1-chloroethyl chloroformate (19.5 mL, 0.179 mol) over 5 min. The mixture was heated at relux for 4 h, cooled to ambient temperature, concentrated, filtered through silica (eluted with 50% diethyl ether/hexanes). The residue was then refluxed in methanol (150 mL) for 45 min and concentrated to afford the hydrochloride salt of the title compound as a light yellow solid (19.2 g, 0.130 mol, 83%): $^1$H NMR (300 MHz, CDCl$_3$) δ 9.47 (brs, 2H), 4.03 (m, 2H), 2.18-2.33 (m, 4H), 1.81-1.89 (m, 2H), 1.55-1.77 (m, 4H).

Example 6B 4-(8-azabicyclo[3.2.1]oct-8-yl)aniline

A mixture of 4-fluoro-nitrobenzene (0.72 mL, 6.8 mmol), the product of Example 6A (1.01 g, 6.82 mmol), and K$_2$CO$_3$ (1.87 g, 13.5 g) in dimethylsulfoxide (7 mL) was heated at 110° C. for 3 hrs. The mixture was diluted with diethyl ether (60 mL) and washed with water (40 mL) and brine (30 mL). The organic layer was dried (Na$_2$SO$_4$), concentrated, and triturated with hexane to give 1.27 g of a yellow solid. A mixture of the solid, HCO$_2$NH$_4$ (1.45 g, 23.0 mmol), and 10% Pd/C (catalytic amount) in methanol (20 mL) was stirred overnight at ambient temperature, filtered, and concentrated. The residue was diluted with sat. aqueous NaHCO$_3$ (20 mL) and extracted with dichloromethane (3×10 mL). The isolated organic layer was dried (Na$_2$SO$_4$), filtered and concentrated to give the title compound as a dark solid (0.665 g, 3.29 mmol, 48%): $^1$H NMR (300 MHz, CDCl$_3$) δ 6.66 (s, 4H), 4.07 (brs, 2H), 3.14 (brs, 2H), 1.74-2.09 (m, 7H), 1.44 (m, 1H), 1.22 (m, 2H).

Example 6C

N-[4-(8-azabicyclo[3.2.1]oct-8-yl)phenyl]-6-(3-chloropyridin-2-yl)-1,2-benzisothiazol-3-amine 1,1-dioxide The title compound was prepared using the procedure as described in Example 1C, substituting the product of Example 6B for 4-tert-butylaniline. MS (ESI$^+$) m/z 479 (M+H)$^+$; (ESI$^-$) m/z 477 (M−H)$^-$; $^1$H NMR (300 MHz, DMSO-d$_6$) δ 1.29 (s, 2H), 1.42 (s, 1H), 1.83 (s, 5H), 1.99 (s, 2H), 4.24 (s, 2H), 6.88 (d, J=8.5 Hz, 1H), 7.56 (dd, J=7.8, 4.1 Hz, 1H), 7.69 (d, J=8.5 Hz, 2H), 8.17 (m, 2H), 8.26 (s, 1H), 8.56 (d, J=8.5 Hz, 1H), 8.71 (d, J=3.4 Hz, 1H), 10.80 (s, 1H).

Example 7

N-(4-chloro-3-fluorophenyl)-6-[3-(trifluoromethyl)pyridin-2-yl]-1,2-benzisothiazol-3-amine 1,1-dioxide

Example 7A 2-(4-methylphenyl)-3-(trifluoromethyl)pyridine

The title compound was prepared using the procedure as described for the preparation of the product of Example 1A, substituting 2-chloro-3-trifluoromethylpyridine for 2,3-dichloropyridine.

Example 7B

6-[3-(trifluoromethyl)pyridin-2-yl]-1,2-benzisothiazol-3-ol 1,1-dioxide

The title compound was prepared using the procedures as described for the preparation of the product of Example 1B, substituting the product of Example 7A for the product of Example 1A. MS (DCI$^+$) m/z 329 (M+H)$^+$; $^1$H NMR (DMSO-d$_6$) δ 7.77 (m, 1H), 7.94 (d, J 7.8, 1H), 8.05 (d, J 7.8, 1H), 8.17 (s, 1H), 8.40 (dd, J 1.3, 7.8, 1H), 8.97 (d, J 4.7, 1H).

Example 7C

N-(4-chloro-3-fluorophenyl)-6-[3-(trifluoromethyl)pyridin-2-yl]-1,2-benzisothiazol-3-amine 1,1-dioxide The title compound was prepared using the procedure as described in Example 1C, substituting the product of Example 7B for the product of Example 1B and substituting 4-chloro-3-fluoroaniline for 4-tert-butylaniline. MS (ESI$^+$) m/z 455 (M+H)$^+$, (ESI$^-$) m/z 453 (M−H)$^-$; $^1$H NMR (DMSO-d$_6$) δ 7.77 (m, 3H), 8.01 (m, 2H), 8.18 (s, 1H), 8.42 (d, J 8.1, 1H), 8.55 (d, J 7.8, 1H), 8.99 (d, J 4.1, 1H), 11.17 (s, 1H).

Example 8

N-[4-(2,2-dichloro-1-methylcyclopropyl)phenyl]-6-[3-(trifluoromethyl)pyridin-2-yl]-1,2-benzisothiazol-3-amine 1,1-dioxide

Example 8A 4-(2,2-dichloro-1-methylcyclopropyl)aniline

Concentrated nitric acid (0.35 mL) was added to (2,2-dichloro-1-methyl-cyclopropyl)-benzene (1.00 g, 4.97 mmol) in acetic anhydride (2 mL) at 0 C. The mixture was stirred for 30 min, allowed to warm to room temperature, stirred for 4 hrs, and partitioned between 1N NaOH and ethyl acetate. The organic layer was separated, dried (Na$_2$SO$_4$), and concentrated, and purified by flash chromatography (5% ethyl acetate/hexanes) to give the nitrophenyl product as a clear oil (0.583 g, 2.37 mmol). A mixture of the isolated oil and SnCl$_2$ (4.71 g, 25 mmol) in methanol (30 mL) and water (0.5 mL) was refluxed for 3hrs, cooled to ambient temperature, concentrated, diluted with sat aq NaHCO$_3$ and ethyl acetate, flitered through Celite®, and separated. The organic layer was washed with brine, dried (Na$_2$SO$_4$), filtered, concentrated, and purified by flash chromatography (25% ethyl acetate/hexanes) to afford the title compound. $^1$H NMR (300 MHz, CDCl$_3$) δ 7.11 (d, 2H), 6.75 (d, 2H), 1.88 (d, 1H), 1.63 (s, 3H), 1.53 (d, 1H).

Example 8B

N-[4-(2,2-dichloro-1-methylcyclopropyl)phenyl]-6-[3-(trifluoromethyl)pyridin-2-yl]-1,2-benzisothiazol-3-amine 1,1-dioxide The title compound was prepared using the procedure as described in Example 1C, substituting the product of Example 7B for the product of Example 1B and substituting the product of Example 8A for 4-tert-butylaniline. MS (DCI$^+$) m/z 526 (M+H)$^+$; $^1$H NMR (DMSO-d$_6$) δ 1.67 (s, 3H), 1.82 (d, J 8.1, 1H), 2.22 (d, J 7.8, 1H), 7.51 (d, J 8.8, 2H), 7.78 (m, 1H), 7.87 (d, J 8.5, 2H), 8.02 (d, J 8.2, 1H), 8.15 (s, 1H), 8.42 (d, J 8.2, 1H), 8.59 (d, J 8.5, 1H), 8.99 (d, J 4.8, 1H), 10.99 (s, 1H).

Example 9

2-[4-({1,1-dioxido-6-[3-(trifluoromethyl)pyridin-2-yl]-1,2-benzisothiazol-3-yl}amino)phenyl]-2-methylpropanenitrile

Example 9A 2-(4-aminophenyl)-2-methylpropanenitrile

A mixture of (4-nitrophenyl)-acetonitrile (4.33 g, 27 mmol), NaOH (3.24 g, 81 mmol), iodomethane (5.5 mL, 88 mmol), and tetrabutylammonium iodide (0.56 g, 1.5 mmol) was stirred in water (35 mL) and dichloromethane (35 mL) for 24 hrs at about 25° C., extracted with dichloromethane, dried (MgSO$_4$), and concentrated. The residue was dissolved in diethyl ether, filtered through Celite®, concentrated, re-filtered through Celite with dichloromethane, and concentrated. This product was dissolved in ethyl acetate, treated with SnCl$_2$ (20 g, 106 mmol). The mixture was stirred overnight at 70° C., concentrated, and partitioned between ethyl acetate and 1 N aqueous NaOH. The organic layer was isolated, washed with brine, dried (Na$_2$SO$_4$), and concentrated to afford the title compound (3.69 g). $^1$H NMR (300 MHz, CDCl$_3$) δ 7.24 (d, 2H), 6.68 (d, 2H), 1.68 (s, 6H).

Example 9B

2-[4-({1,1-dioxido-6-[3-(trifluoromethyl)pyridin-2-yl]-1,2-benzisothiazol-3-yl}amino phenyl]-2-methyl-propanenitrile The title compound was prepared using the procedure as described in Example 1C, substituting the product of Example 7B for the product of Example 1B and substituting the product of Example 9A for 4-tert-butylaniline. MS (DCI$^+$) m/z 471 (M+H)$^+$ (90%), m/z 488 (M+NH$_4$)$^+$ (100%); $^1$HNMR (DMSO-d$_6$) δ 1.73 (s, 6H), 7.67 (d, J 8.8, 2H), 7.78 (dd, J 5.1, 7.8, 1H), 7.93 (d, J 8.5, 2H), 8.02 (d, J 8.5, 1H), 8.15 (s, 1H), 8.42 (dd, J 1.3, 8.1, 1H), 8.60 (d, J 8.1, 1H), 8.99 (d, J 3.8, 1H), 11.06 (s, 1H).

Example 10

N-(4-chlorophenyl)-6-[3-(trifluoromethyl)pyridin-2-yl]-1,2-benzisothiazol-3-amine 1,1-dioxide The title compound was prepared using the procedure as described in Example 1C, substituting the product of Example 7B for the product of Example 1B and substituting 4-chloroaniline for 4-tert-butylaniline. MS (DCI$^+$) m/z 438 (M+H)$^+$ (32%), m/z 252 (M-185)$^+$ (100%); $^1$H NMR (DMSO-d$_6$) δ 7.58 (d, J 8.9, 2H), 7.78 (dd, J 4.7, 7.1, 1H), 7.92 (d, J 9.1, 2H), 8.01 (d, J 7.8, 1H), 8.15 (s, 1H), 8.41 (dd, J 1.7, 8.2, 1H), 8.57 (d, J 9.5, 1H), 8.98 (d, J 4.0, 1H), 11.05 (s, 1H).

Example 11

N-[4-(trifluoromethyl)phenyl]-6-[3-(trifluoromethyl)pyridin-2-yl]-1,2-benzisothiazol-3-amine 1,1-dioxide The title compound was prepared by using the procedure as described in Example 1C, substituting the product of Example 7B for the product of Example 1B and substituting 4-trifluoromethylaniline for 4-tert-butylaniline. MS (DCI$^+$) m/z 472 (M+H)$^+$ (40%), m/z 489 (M+NH$_4$)$^+$ (100%); $^1$H NMR (DMSO-d$_6$) δ 7.78 (dd, J 5.1, 8.1, 1H), 7.90 (d, J 8.5, 2H), 8.04 (d, J 7.5, 1H), 8.13 (d, J 8.2, 2H), 8.18 (s, 1H), 8.42 (d, J 8.1, 1H), 8.62 (d, J 8.8, 1H), 8.99 (d, J 4.1, 1H), 11.20 (s, 1H).

Example 12

N-(4-tert-butylphenyl)-6-[3-(trifluoromethyl)pyridin-2-yl]-1,2-benzisothiazol-3-amine 1,1-dioxide The title compound was prepared using the procedure as described in Example 1C, substituting the product of Example 7B for the product of Example 1B. MS (DCI$^+$) m/z 460 (M+H)$^+$; $^1$H NMR (DMSO-d$_6$) δ 1.32 (s, 9H), 7.53 (d, J 6.8, 2H), 7.78 (m, 3H), 8.01 (d, J 8.2, 1H), 8.13 (s, 1H), 8.42 (d, J 8.2, 1H), 8.59 (d, J 8.1, 1H), 8.99 (d, J 4.8, 1H), 10.95 (s, 1H).

Example 13

N-(4-azepan-1-ylphenyl)-6-[3-(trifluoromethyl)pyridin-2-yl]-1 2-benzisothiazol-3-amine 1,1-dioxide

Example 13A 4-azepan-1-ylaniline

The title compound was prepared using the procedures as described in Examples 6A and 6B, substituting hexamethyleneimine for tropane. $^1$H NMR (300 MHz, CDCl$_3$) δ 6.65 (d, 2H), 6.57 (d, 2H), 3.38 (t, 4H), 1.71-1.80 (m, 4H), 1.50-1.55 (m, 4H).

Example 13B

N-(4-azepan-1-ylphenyl)-6-[3-(trifluoromethyl)pyridin-2-yl]-1,2-benzisothiazol-3-amine 1,1-dioxide The title compound was prepared using the procedure as described in Example 1C, substituting the product of Example 7B for the product of Example 1B, and substituting the product of Example 13A for 4-tert-butylaniline. MS (DCI$^+$) m/z 501 (M+H)$^+$ (30%), m/z 310 (M-190)$^+$ (100%); $^1$H NMR (DMSO-d$_6$) δ 1.48 (m, 4H), 1.75 (bs, 4H), 3.49 (t, J 6.1, 4H), 6.79 (d, J 9.5, 2H), 7.65 (d, J 9.2, 2H), 7.77 (dd, J 5.1, 7.8, 1H), 7.97 (d, J 8.8, 1H), 8.08 (s, 1H), 8.41 (d, J 8.1, 1H), 8.54 (d, J 8.2, 1H), 8.98 (d, J 4.7, 1H), 10.78 (s, 1H).

Example 14

6-[3-(trifluoromethyl)pyridin-2-yl]-N-[6-(trifluoromethyl)pyridin-3-yl]-1 2-benzisothiazol-3-amine 1,1-dioxide The title compound was prepared using the procedure as described in Example 1C, substituting the product of Example 7B for the product of Example 1B, and substituting 6-trifluoromethyl-pyridin-3-ylamine for 4-tert-butylaniline. MS (DCI$^+$) m/z 473 (M+H)$^+$ (4%), m/z 252 (M-220)$^+$ (100%); $^1$H NMR (DMSO-d$_6$) δ 7.79 (dd, J 4.7, 8.1, 1H), 8.08 (t, J 8.5, 2H), 8.21 (s, 1H), 8.42 (d, J 8.1, 1H), 8.59 (d, J 8.2, 1H), 8.66 (dd, J 2.0, 8.5, 1H), 8.99 (d, J 4.0, 1H), 9.16 (d, J 2.4, 1H), 11.44 (s, 1H).

Example 15

N-(2,2-difluoro-1,3-benzodioxol-5-yl)-6-[3-(trifluoromethyl)pyridin-2-yl]-1,2-benzisothiazol-3-amine 1,1-dioxide The title compound was prepared using the procedure as described in Example 1C, substituting the product of Example 7B for the product of Example 1B, and substituting 2,2-difluoro-benzo[1,3]dioxol-5-ylamine for 4-tert-butylaniline. MS (DCI$^+$) m/z 484 (M+H)$^+$; $^1$H NMR (DMSO-d$_6$) δ 7.56 (d, J 8.8, 1H), 7.65 (dd, J 2.3, 8.8, 1H), 7.78 (dd, J 4.7, 8.1, 1H), 7.94 (d, J 2.3, 1H), 8.03 (d, J 8.2, 1H), 8.16 (s, 1H), 8.42 (d, J 8.1, 1H), 8.55 (d, J 8.2, 1H), 8.99 (d, J 4.8, 1H), 11.14 (s, 1H).

Example 16

N-[4-(methylsulfonyl)phenyl]-6-[3-(trifluoromethyl)pyridin-2-yl]-1 2-benzisothiazol-3-amine 1,1-dioxide The title compound was prepared using the procedure as described in Example 1C, substituting the product of Example 7B for the product of Example 1B, and substituting 4-methanesulfonyl-aniline for 4-tert-butylaniline. MS (DCI$^+$) m/z 482 (M+H)$^+$ (7%), m/z 252 (M-229)$^+$ (100%); $^1$H NMR (DMSO-d$_6$) δ 3.25 (s, 3H), 7.79 (dd, J 4.7, 8.1, 1H), 8.06 (m, 3H), 8.17 (m, 3H), 8.42 (d, J 8.2, 1H), 8.63 (d, J 8.2, 1H), 8.99 (d, J 4.8, 1H), 11.25 (s, 1H).

Example 17

N-[4-(azepan-1-ylsulfonyl)phenyl]-6-[3-(trifluoromethyl)pyridin-2-yl]-1,2-benzisothiazol-3-amine 1,1-dioxide

Example 17A

4-(azepan-1-ylsulfonyl)aniline

A mixture of 4-nitrobenzenesulfonyl chloride (1.78 g, 8.0 mmol), pyridine (0.78 mL, 9.6 mmol), and hexamethyleneimine (0.796 g, 8.02 mmol) in dichloromethane (22 mL) was stirred for 5 hrs at 0° C., diluted with 1N HCl, and extracted with dichloromethane. The organic layer was dried (Na$_2$SO$_4$), filtered, concentrated, and triturated with diethyl ether to give 1-(4-nitro-benzenesulfonyl)-azepane as a brown solid. The solid was added to a mixture of HCO$_2$NH$_4$ (1.91 g, 30.3 mmol) and 10% Pd/C (catalytic amount) in methanol (20 mL) and ethyl acetate (4 mL), stirred overnight at about 25° C., filtered, concentrated, diluted with water, and extracted with dichloromethane. The isolated organic layer was dried (Na$_2$SO$_4$), filtered and concentrated to give the title compound. $^1$H NMR (300 MHz, CDCl$_3$) δ 8.35 (d, 2H), 7.97 (d, 2H), 3.31 (t, 4H), 1.70-1.79 (m, 4H), 1.56-1.63 (m, 4H).

Example 17B

N-[4-(azepan-1-ylsulfonyl)phenyl]-6-[3-(trifluoromethyl)pyridin-2-yl]-1,2-benzisothiazol-3-amine 1,1-dioxide The title compound was prepared using the procedure as described in Example 1C, substituting the product of Example 7B for the product of Example 1B, and substituting the product of Example 17A for 4-tert-butylaniline. MS (DCI$^+$) m/z 565 (M+H)$^+$ (6%), m/z 252 (M-312)$^+$ (100%); $^1$H NMR (DMSO-d$_6$) δ 1.52 (m, 4H), 1.65 (bs, 4H), 3.24 (t, J 5.7, 4H), 7.78 (dd, J 4.8, 7.5, 1H), 7.93 (d, J 8.9, 2H), 8.04 (d, J 8.2, 1H), 8.13 (d, J 8.8, 2H), 8.18 (s, 1H), 8.42 (d, J 8.1, 1H), 8.62 (d, J 7.8, 1H), 8.99 (d, J 4.0, 1H), 11.20 (s, 1H).

Example 18

1-[4-({1,1-dioxido-6-[3-(trifluoromethyl)pyridin-2-yl]-1,2-benzisothiazol-3-yl}amino)phenyl]ethanone The title compound was prepared using the procedure as described in Example 1C, substituting the product of Example 7B for the product of Example 1B, and substituting 4'-aminoacetophenone for 4-tert-butylaniline. MS (DCI$^+$) m/z 446 (M+H)$^+$ (50%), m/z 252 (M-193)$^+$ (100%); $^1$H NMR (DMSO-d$_6$) δ 2.61 (s, 3H), 7.78 (dd, J 5.1, 8.2, 1H), 8.06 (m, 5H), 8.18 (s, 1H), 8.42 (d, J 8.1, 1H), 8.63 (d, J 8.2, 1H), 8.99 (d, J 4.7, 1H), 11.16 (s, 1H).

Example 19

N-[4-(8-azabicyclo[3.2.1]oct-8-yl)-3,5-difluorophenyl]-6-[3-(trifluoromethyl)pyridin-2-yl]-1,2-benzisothiazol-3-amine 1,1-dioxide

Example 19A

4-(8-Aza-bicyclo[3.2.1]oct-8-yl)-3,5-difluoro-phenylamine

The title compound was prepared using the procedure as described for the preparation of the product of Example 6B, substituting 3,4,5-trifluoronitrobenzene for 4-fluronitrobenzene. $^1$H NMR (300 MHz, CDCl$_3$) δ 6.17(d, 2H), 3.90 (brs, 2H), 3.50 (brs, 2H), 1.36-2.03 (m, 10H).

Example 19B

N-[4-(8-azabicyclo[3.2.1]oct-8-yl)-3,5-difluorophenyl]-6-[3-(trifluoromethyl)pyridin-2-yl-1,2-benzisothiazol-3-amine 1,1-dioxide The title compound was prepared using the procedure as described in Example 1C, substituting the product of Example 7B (0.1320 g, 0.403 mmol) for the product of Example 1B and substituting the product of Example 19A (0.2306 g, 0.968 mmol) for 4-tert-butylaniline. MS (ESI$^+$) m/z 549 (M+H)$^+$, m/z 547 (M−H)$^-$; $^1$H NMR (CD$_3$OD) δ 1.53 (m, 3H), 1.92 (m, 7H), 4.16 (bs, 2H), 7.54 (d, J 12.9, 2H), 7.72 (dd, J 5.1, 7.8, 1H), 7.94 (d, J 8.1, 1H), 8.06 (s, 1H), 8.35 (d, J 8.2, 2H), 8.91 (d, J 4.8, 1H).

Example 20

6-[3-(trifluoromethyl)pyridin-2-yl]-N-{4-[(trifluoromethyl)sulfonyl]phenyl}-1,2-benzisothiazol-3-amine 1,1-dioxide The title compound was prepared using the procedure of Example 1C, substituting the product of Example 7B (0.1476 g, 0.450 mmol) for the product of Example 1B and substituting 4-aminophenyl trifluoromethyl sulphone (0.2571 g, 1.14 mmol) for 4-tert-butylaniline. MS (ESI$^+$) m/z 536 (M+H)$^+$, m/z 534 (M−H)$^-$; $^1$H NMR (CD$_3$OD) δ 7.73 (dd, J 4.7, 8.1, 1H), 7.99 (d, J 8.2, 1H), 8.12 (s, 1H), 8.19 (d, J 9.2, 2H), 8.38 (m, 3H), 8.46 (d, J 7.8, 1H), 8.92 (d, J 4.4, 1H).

Example 21

N-[4-(8-azabicyclo[3.2.1]oct-8-yl)-3-fluorophenyl]-6-[3-(trifluoromethyl)pyridin-2-yl]-1,2-benzisothiazol-3-amine 1,1-dioxide

Example 21A 4-(8-Aza-bicyclo[3.2.1]oct-8-yl)-3-fluoro-phenylamine

The title compound was prepared using the procedure as described for the preparation of the product of Example 6B, substituting 3,4-difluoronitrobenzene for 4-fluoronitrobenzene $^1$H NMR (300 MHz, CDCl$_3$) δ 6.69 (m, 1H), 6.40 (m, 2H), 4.00 (brs, 2H), 3.42 (brs, 2H), 1.86-2.03 (m, 4H), 1.65-1.77 (m, 3H), 1.32-1.57 (m, 3H).

Example 21B

N-[4-(8-azabicyclo[3.2.1]oct-8-yl)-3-fluorophenyl]-6-[3-(trifluoromethyl)pyridin-2-yl]-1,2-benzisothiazol-3-amine 1,1-dioxide The title compound was prepared using the procedure as described in Example 1C, substituting the product of Example 7B for the product of Example 1B, and substituting the product of Example 21A for 4-tert-butylaniline. MS (DCI$^+$) m/z 531 (M+H)$^+$; $^1$H NMR (DMSO-d$_6$) δ 1.42 (m, 3H), 1.79 (m, 5H), 1.98 (m, 2H), 4.23 (bs, 2H), 7.09 (t, J 9.5 1H), 7.53 (dd, J 2.1, 8.5, 1H), 7.74 (m, 2H), 8.00 (d, J 7.8, 1H), 8.12 (s, 1H), 8.41 (d, J 7.8, 1H), 8.54 (d, J 8.1, 1H), 8.98 (d, J 4.7, 1H), 10.92 (s, 1H).

Example 22

N-[4-(trifluoromethoxy)phenyl]-6-[3-(trifluoromethyl)pyridin-2-yl]-1,2-benzisothiazol-3-amine 1,1-dioxide The title compound was prepared using the procedure as described in Example 1C, substituting the product of Example 7B for the product of Example 1B, and substituting 4-trifluoromethoxy aniline for 4-tert-butylaniline. MS (DCI$^+$) m/z 488 (M+H)$^+$ (50%), m/z 309 (M-177)$^+$ (100%); $^1$H NMR (DMSO-d$_6$) δ 7.53 (d, J 8.5, 2H), 7.78 (dd, J 5.1, 7.2, 1H), 8.01 (m, 3H), 8.15 (s, 1H), 8.42 (d, J 8.1, 1H), 8.57 (d, J 7.1, 1H), 8.99 (d, J 4.7, 1H), 11.11 (s, 1H).

Example 23

N-[4-(8-azabicyclo[3.2.1]oct-8-ylsulfonyl)phenyl]-6-[3-(trifluoromethyl)pyridin-2-yl]-1,2-benzisothiazol-3-amine 1,1-dioxide

Example 23A 4-(8-aza-bicyclo[3.2.1]octane-8-sulfonyl)-phenylamine

A mixture of 4-nitrobenzenesulfonyl chloride (1.78 g, 8.0 mmol), pyridine (0.78 mL, 9.6 mmol), and 8-azabicyclo[3.2.1]octane (0.796 g, 8.02 mmol) in dichloromethane (22 mL) was stirred for 5 hrs at 0° C., diluted with 1N HCl, and extracted with dichloromethane. The isolated organic layer was dried (Na$_2$SO$_4$), filtered, concentrated, and triturated with diethyl ether to give 1-(4-nitro-benzenesulfonyl)-8-azabicyclo[3.2.1]octane as a brown solid. The solid was added to a mixture of HCO$_2$NH$_4$ (1.91 g, 30.3 mmol) and 10% Pd/C (catalytic amount) in methanol (20 mL) and ethyl acetate (4 mL), stirred overnight at about 25° C., filtered, concentrated, diluted with water, and extracted with dichloromethane. The isolated organic layer was dried (Na$_2$SO$_4$), filtered and concentrated to give the title compound. $^1$H NMR (300 MHz, CDCl$_3$) δ 7.74 (d, 2H), 7.02 (d, 2H), 4.17 (brs, 2H), 1.42-1.86 (m, 10H).

Example 23B

N-[4-(8-azabicyclo[3.2.1]oct-8-ylsulfonyl)phenyl]-6-[3-(trifluoromethyl)pyridin-2-yl]-1,2-benzisothiazol-3-amine 1,1-dioxide The title compound was prepared using the procedure as described in Example 1C, substituting the product of Example 7B for the product of Example 1B, and substituting the product of Example 23A for 4-tert-butylaniline. MS (ESI$^+$) m/z 253 (M-323)$^+$ (100%) m/z 577 (M+H)$^+$ (20%); $^1$H NMR (300 MHz, DMSO-d$_6$) δ 1.29 (m, 2H), 1.50 (m, 6H), 1.67 (m, 2H), 4.17 (s, 2H), 7.78 (dd, J=7.6, 4.6 Hz, 2H), 8.01 (m, 2H), 8.12 (m, 2H), 8.18 (s, 1H), 8.41 (d, J=8.1 Hz, 1H), 8.62 (d, J=8.1 Hz, 1H), 8.99 (d, J=4.7 Hz, 1H), 11.20 (s, 1H).

Example 24

N-(4-tert-butylphenyl)-6-pyrimidin-2-yl-1,2-benzisothiazol-3-amine 1,1-dioxide

Example 24A 6-pyrimidin-2-yl-1,2-benzisothiazol-3-ol 1,1-dioxide

The title compound was prepared using the procedures as described in Examples 1A and 1B, substituting 2-chloropyrimidine for 2,3-dichloropyridine. MS (APCI$^+$) m/z 262 (M+H)$^+$; $^1$H NMR (300 MHz, DMSO-d$_6$) δ ppm 7.60 (t, J=4.7 Hz, 1H), 8.07 (d, J=7.8 Hz, 1H), 8.79 (s, 1H), 8.82 (dd, J=8.0, 1.5 Hz, 1H), 9.02 (d, J=4.7 Hz, 2H).

Example 24B

N-(4-tert-butylphenyl)-6-pyrimidin-2-yl-1,2-benzisothiazol-3-amine 1,1-dioxide

The title product was prepared using the procedure as described in Example 1C, substituting the product of Example 24A for the product of Example 1B. MS (ESI$^+$) m/z 393 (M+H)$^+$, m/z 391 (M−H)$^-$; $^1$H NMR (300 MHz, DMSO-d$_6$) δ 1.32 (s, 9H), 7.53 (d, J=8.8 Hz, 2H), 7.61 (t, J=4.9 Hz, 1H), 7.80 (d, J=8.5 Hz, 2H), 8.66 (d, J=8.5 Hz, 1H), 8.80 (s, 1H), 8.90 (dd, J=8.1, 1.4 Hz, 1H), 9.04 (d, J=5.1 Hz, 2H), 11.00 (s, 1H).

Example 25

6-pyrimidin-2-yl-N-{4-[(trifluoromethyl)sulfonyl]phenyl}-1,2-benzisothiazol-3-amine 1,1-dioxide The title product was prepared using the procedure as described in Example 1C, substituting the product of Example 24A for the product of Example 1B, and substituting 4-trifluoromethanesulfonyl-phenylamine for 4-tert-butylaniline. $^1$H NMR (300 MHz, DMSO-d$_6$) δ 7.63 (t, J=4.9 Hz, 1H), 8.29 (m, 2H), 8.39 (m, 2H), 8.70 (d, J=8.1 Hz, 1H), 8.86 (s, 1H), 8.95 (dd, J=8.1, 1.4 Hz, 1H), 9.05 (d, J=5.1 Hz, 2H), 11.46 (s, 1H).

Example 26

6-[3-(trifluoromethyl)pyridin-2-yl]-N-[5-(trifluoromethyl)pyridin-2-yl]-1,2-benzisothiazol-3-amine 1,1-dioxide The title compound was prepared using the procedure as described in Example 1C, substituting the product of Example 7B for the product of Example 1B, and substituting 2-amino-5-trifluoromethylpyridine for 4-tert-butylaniline. $^1$H NMR (300 MHz, CDCl$_3$) δ 8.92 (d, 1H), 8.72 (d, 1H), 8.67 (s, 1H), 8.45 (brs, 1H), 8.15-8.19 (m, 2H), 8.11 (dd, 1H), 7.95 (d, 1H), 7.89 (d, 1H), 7.57 (dd, 1H). MS (m/z) 473.1.

5) Biological Activity

In Vitro Data—Determination of Inhibition Potencies (a) In Vitro Data—Determination of Inhibition Potencies Dulbecco's modified Eagle medium (D-MEM)(with 4.5 mg/mL glucose) and fetal bovine serum were obtained from Hyclone Laboratories, Inc. (Logan, Utah). Dulbecco's phosphate-buffered saline (D-PBS)(with 1 mg/mL glucose and 3.6 mg/l Na pyruvate)(without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNAs for the human VR1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. *Pain* Vol 88, pages 205-215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with growth medium containing 800 µg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 µg/mL G418 (Cal-biochem) and 10% fetal bovine serum under a humidified 5% CO$_2$ atmosphere.

The functional activity of compounds at the VR1 receptor was determined with a Ca$^{2+}$ influx assay and measurement of intracellular Ca$^{2+}$ levels ([Ca$^{2+}$]i). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the VR1 agonist capsaicin was also prepared in D-PBS. The fluorescent Ca$^{2+}$ chelating dye fluo-4 was used as an indicator of the relative levels of [Ca$^{2+}$]i in a 96-well format using a Fluorescence Imaging Plate Reader (FLIPR)(Molecular Devices, Sunnyvale, Calif.). Cells were grown to confluence in 96-well black-walled tissue culture plates. Then, prior to the assay, the cells were loaded with 100 µL per well of fluo-4 AM (2 µM, in D-PBS) for 1-2 hours at 23° C. Washing of the cells was performed to remove extracellular fluo-4 AM (2×1 mL D-PBS per well), and afterward, the cells were placed in the reading chamber of the FLIPR instrument 50 µL of the compound solutions were added to the cells at the 10th second time mark of the experimental run. Then, after a 3-minute time delay, 50 µL of the capsaicin solution was added at the 190-second time mark (0.05 µM final concentration) (final volume=200 µL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190th second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and IC$_{50}$ values were calculated.

The compounds of the present invention were found to be antagonists of the vanilloid receptor subtype 1 (VR1) receptor with IC$_{50s}$ from 0.02 µM to 2.2 µM (26 compounds tested).

(b) In Vivo Data—Determination of Antinociceptive Effect

Experiments were performed on adult male 129J mice (Jackson laboratories, Bar Harbor, Me.), weighing 20-25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the completion of the experiment. All animal handling and experimental procedures were approved by an IACUC Committee.

The antinociceptive test used was a modification of the abdominal constriction assay described in Collier, et al., *Br. J. Pharmacol. Chemother*. Vol. 32 pages 295-310 (1968). Each animal received an intraperitoneal (i.p.) injection of 0.3 mL of 0.6% acetic acid in normal saline to evoke writhing. Animals were placed separately under clear cylinders for the observation and quantification of abdominal constriction. Abdominal constriction was defined as a mild constriction and elongation passing caudally along the abdominal wall, accompanied by a slight twisting of the trunk and followed by bilateral extension of the hind limbs. The total number of abdominal constrictions was recorded from 5 to 20 minutes after acetic acid injection. The ED$_{50s}$ were determined based on the i.p. injection.

The other antinociceptive test used was Complete Freund's Adjuvant-induced Thermal Hyperalgesia (CFA) assay described in Pircio et al. *Eur J Pharmacol*. Vol. 31(2) pages 207-215 (1975). Chronic inflammatory hyperalgesia was induced in one group of rats following the injection of complete Freund's adjuvant (CFA, 50%, 150 µL) into the plantar surface of the right hindpaw 48 hours prior to testing. Thermal nociceptive thresholds were measured in three different groups of rats. The ED$_{50s}$ were determined based on the oral administration. The $ED_{50}$ values for three compounds tested were in the range of 30 and 72 µmol/kg.

The in vitro and in vivo data demonstrates that compounds of the present invention antagonize the VR1 receptor and are useful for treating pain.

Compounds of the present invention, as VR1 antagonists, are also useful for ameliorating or preventing additional disorders that are affected by the VR1 receptors such as, but not limited to, inflammatory thermal hyperalgesia, bladder overactivity, and urinary incontinence.

Compounds of the present invention, including but not limited to those specified in the examples, can be used to treat pain as demonstrated by Nolano, M. et al., Pain Vol. 81 pages 135-145 (1999); Caterina, M. J. and Julius, D., Annu. Rev. Neurosci. Vol. 24, pages 487-517 (2001); Caterina, M. J. et al., Science Vol. 288 pages 306-313 (2000); Caterina, M. J. et al., Nature Vol. 389, pages 816-824 (1997).

Compounds of the present invention, including but not limited to those specified in the examples, can be used to treat bladder overactivity and/or urinary incontinence as demonstrated by Fowler, C. Urology Vol. 55 pages 60-64 (2000).

Compounds of the present invention, including but not limited to those specified in the examples, can be used to treat inflammatory thermal hyperalgesia as demonstrated by Davis, J. et al., Nature Vol. 405 pages 183-187 (2000).

The present invention also provides pharmaceutical compositions that comprise compounds of the present invention. The pharmaceutical compositions comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water, isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form.

Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals, which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), Poste et al., Chapter 4, p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants that may be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s), which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder, activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (*J. Pharmaceutical Sciences* Vol. 66 pages 1 et seq (1977). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug," as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood.

The present invention contemplates compounds of formula I formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.01 to about 100 mg/kg/day. For purposes of oral administration, more preferable doses can be in the range of from about 0.1 to about 25 mg/kg/day. If desired, the effective daily dose can be divided into multiple doses for purposes of administration; consequently, single dose compositions may contain such amounts or submultiples thereof to make up the daily dose.

Compounds of the present invention were named by ACD/ChemSketch version 5.0 (developed by Advanced Chemistry Development, Inc., Toronto, ON, Canada) or were given names, which appeared to be consistent with ACD nomenclature.

What is claimed is:

1. A compound of formula (I)

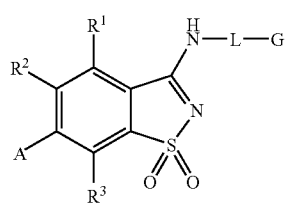

or a pharmaceutically acceptable salt, prodrug, salt of a prodrug thereof, wherein $R^1$, $R^2$ and $R^3$ are independently selected from the group consisting of hydrogen, halogen, alkyl and haloalkyl;

L is a bond or $C_{1-6}$ alkyl;

A is a ring selected from the group consisting of cycloalkyl, cycloalkenyl, heterocycle, aryl and heteroaryl; wherein each A is independently substituted with 0, 1, 2, 3, 4 or 5 substituents selected from the group consisting of alkyl, halogen, cyano, hydroxyl, alkoxy, haloalkoxy, —SH, —S(alkyl), —S(O)alkyl, —S(O)$_2$alkyl, —S(O)$_2$NH$_2$, —S(O)$_2$N(H)alkyl, —S(O)$_2$N(alkyl)$_2$, —NH$_2$, —N(H)alkyl, —N(alkyl)$_2$, —C(O)OH, —C(O)O(alkyl), —C(O)alkyl, —C(O)NH$_2$, —C(O)N(H)alkyl, —C(O)N(alkyl)$_2$, cyanoalkyl, hydroxyalkyl, alkoxyalkyl, haloalkoxyalkyl, -alkylSH, -alkylS(alkyl), -alkylS(O)alkyl, -alkylS(O)$_2$alkyl, -alkylS(O)$_2$NH$_2$, -alkylS(O)$_2$N(H)alkyl, -alkylS(O)$_2$N(alkyl)$_2$, -alkylNH$_2$, -alkylN(H)alkyl, -alkylN(alkyl)$_2$, -alkylC(O)OH, -alkylC(O)O(alkyl), -alkylC(O)alkyl, -alkylC(O)NH$_2$, -alkylC(O)N(H)alkyl, and -alkylC(O)N(alkyl)$_2$;

G is an aryl ring; wherein each G is independently substituted with 0, 1, 2, 3, 4 or 5 substituents selected from the group consisting of cyano, —OR$_a$, —OC(O)R$_a$, —OC(O)NR$_a$R$_b$, —SR$_a$, —S(O)R$_a$, —S(O)$_2$R$_a$, —S(O)$_2$NR$_a$R$_b$, —NR$_a$R$_b$, —C(O)OR$_a$, —C(O)R$_a$, —C(O)NR$_a$R$_b$, R$_c$, haloalkyl, cyanoalkyl, -alkylOR$_a$, -alkylOC(O)R$_a$, -alkylOC(O)NR$_a$R$_b$, -alkylSR$_a$, -alkylS(O)R$_a$, -alkylS(O)$_2$R$_a$, -alkylS(O)$_2$NR$_a$R$_b$, -alkylNR$_a$R$_b$, -alkylC(O)OR$_a$, -alkylC(O)R$_a$, -alkylC(O)NR$_a$R$_b$, and -alkyl-R$_c$;

wherein R$_a$, at each occurrence, is independently selected from the group consisting of hydrogen, alkyl, haloalkyl, cycloalkyl, cycloalkenyl, heterocycle, aryl, heteroaryl, arylalkyl and heteroarylalkyl; wherein the cycloalkyl, cycloalkenyl, heterocycle, aryl, heteroaryl, aryl moiety of the arylalkyl and the heteroaryl moiety of the heteroarylalkyl are independently substituted with 0, 1, 2, 3, 4 or 5 substituents selected from the group consisting of alkyl, halogen, haloalkyl, cyanoalkyl, hydroxyl, alkoxy, haloalkoxy, hydroxyalkyl, alkoxyalkyl, haloalkoxyalkyl, —SH, —S(alkyl), —S(O)alkyl, —S(O)$_2$alkyl, —S(O)$_2$NH$_2$, —S(O)$_2$N(H)alkyl, —S(O)$_2$N(alkyl)$_2$, —NH$_2$, —N(H)alkyl, —N(alkyl)$_2$, —C(O)OH, —C(O)O(alkyl)—C(O)O(aryl), —C(O)alkyl, —C(O)NH$_2$, —C(O)N(H)alkyl, and —C(O)N(alkyl)$_2$;

wherein R$_b$, at each occurrence, is independently selected from the group consisting of hydrogen, alkyl, cycloalkyl, aryl, heterocycle, heteroaryl, arylalkyl and heteroarylalkyl; wherein each of the cycloalkyl, aryl, heterocycle, heteroaryl, aryl moiety of the arylalkyl and heteroaryl moiety of the heteroarylalkyl is independently substituted with 0, 1, 2, 3, 4 or 5 substituents selected from the group consisting of alkyl, halogen, haloalkyl, cyanoalkyl, hydroxyl, alkoxy, haloalkoxy, hydroxyalkyl, alkoxyalkyl, haloalkoxyalkyl, —SH, —S(alkyl), —S(O)alkyl, —S(O)$_2$alkyl, —S(O)$_2$NH$_2$, —S(O)$_2$N(H)alkyl, —S(O)$_2$N(alkyl)$_2$, —NH$_2$, —N(H)alkyl, —N(alkyl)$_2$, —C(O)OH, —C(O)O(aryl), —C(O)alkyl, —C(O)NH$_2$, —C(O)N(H)alkyl, and —C(O)N(alkyl)$_2$; and wherein R$_c$, at each occurrence, is a ring independently selected from the group consisting cycloalkyl, cycloalkenyl, heterocycle, aryl and heteroaryl; wherein each R$_c$ is independently substituted with 0, 1, 2, 3, 4 or 5 substituents selected from the group consisting of alkyl, halogen, cyano, hydroxyl, alkoxy, haloalkoxy, —SH, —S(alkyl), —S(O)alkyl, —S(O)$_2$alkyl, —S(O)$_2$NH$_2$, —S(O)$_2$N(H)alkyl, —S(O)$_2$N(alkyl)$_2$, —NH$_2$, —N(H)alkyl, —N(alkyl)$_2$, —C(O)OH, —C(O)O(alkyl), —C(O)alkyl, —C(O)NH$_2$, —C(O)N(H)alkyl, —C(O)N(alkyl)$_2$; haloalkyl, cyanoalkyl, hydroxyalkyl, alkoxyalkyl, haloalkoxyalkyl, -alkylSH, -alkylS(alkyl), -alkylS(O)alkyl, -alkylS(O)$_2$alkyl, -alkylS(O)$_2$NH$_2$, -alkylS(O)$_2$N(H)alkyl, -alkylS(O)$_2$N(alkyl)$_2$, -alkylNH$_2$, -alkylN(H)alkyl, -alkylN(alkyl)$_2$, -alkylC(O)OH, -alkylC(O)O(alkyl), -alkylC(O)alkyl, -alkylC(O)NH$_2$, -alkylC(O)N(H)alkyl, and -alkylC(O)N(alkyl)$_2$.

2. The compound of claim 1, wherein A is heteroaryl.
3. The compound of claim 2, wherein A is pyridyl.
4. The compound of claim 3, wherein L is a bond.
5. The compound of claim 4, wherein G is aryl.
6. The compound of claim 5, wherein G is phenyl.
7. The compound of claim 6, wherein the compound is selected from the group consisting of
N-(4-tert-butylphenyl)-6-(3-chloropyridin-2-yl)-1,2-benzisothiazol-3-amine 1,1-dioxide;
6-(3-chloropyridin-2-yl)-N-{4-[(trifluoromethyl)sulfonyl]phenyl}-1,2-benzisothiazol-3-amine 1,1-dioxide;
1-(4-{[6-(3-chloropyridin-2-yl)-1,1-dioxido-1,2-benzisothiazol-3-yl]amino}phenyl)ethanone;
N-[4-(8-azabicyclo[3.2.1]oct-8-yl)phenyl]-6-(3-chloropyridin-2-yl)-1,2-benzisothiazol-3-amine 1,1-dioxide;
N-(4-chloro-3-fluorophenyl)-6-[3-(trifluoromethyl)pyridin-2-yl]-1,2-benzisothiazol-3-amine 1,1-dioxide;
N-[4-(2,2-dichloro-1-methylcyclopropyl)phenyl]-6-[3-(trifluoromethyl)pyridin-2-yl]-1,2-benzisothiazol-3-amine 1,1-dioxide;
2-[4-({1,1-dioxido-6-[3-(trifluoromethyl)pyridin-2-yl]-1,2-benzisothiazol-3-yl}amino)phenyl]-2-methylpropanenitrile;
N-(4-chlorophenyl)-6-[3-(trifluoromethyl)pyridin-2-yl]-1,2-benzisothiazol-3-amine 1,1-dioxide;
N-[4-(trifluoromethyl)phenyl]-6-[3-(trifluoromethyl)pyridin-2-yl]-1,2-benzisothiazol-3-amine 1,1-dioxide;
N-(4-tert-butylphenyl)-6-[3-(trifluoromethyl)pyridin-2-yl]-1,2-benzisothiazol-3-amine 1,1-dioxide;
N-(4-azepan-1-ylphenyl)-6-[3-(trifluoromethyl)pyridin-2-yl]-1,2-benzisothiazol-3-amine 1,1-dioxide;
N-[4-(methylsulfonyl)phenyl]-6-[3-(trifluoromethyl)pyridin-2-yl]-1,2-benzisothiazol-3-amine 1,1-dioxide;
N-[4-(azepan-1-ylsulfonyl)phenyl]-6-[3-(trifluoromethyl)pyridin-2-yl]-1,2-benzisothiazol-3-amine 1,1-dioxide;
1-[4-({1,1-dioxido-6-[3-(trifluoromethyl)pyridin-2-yl]-1,2-benzisothiazol-3-yl}amino)phenyl]ethanone;
N-[4-(8-azabicyclo[3.2.1]oct-8-yl)-3,5-difluorophenyl]-6-[3-(trifluoromethyl)pyridin-2-yl]-1,2-benzisothiazol-3-amine 1,1-dioxide;
6-[3-(trifluoromethyl)pyridin-2-yl]-N-{4-[(trifluoromethyl)sulfonyl]phenyl}-1,2-benzisothiazol-3-amine 1,1-dioxide;
N-[4-(8-azabicyclo[3.2.1]oct-8-yl)-3-fluorophenyl]-6-[3-(trifluoromethyl)pyridin-2-yl]-1,2-benzisothiazol-3-amine 1,1-dioxide;
N-[4-(trifluoromethoxy)phenyl]-6-[3-(trifluoromethyl)pyridin-2-yl]-1,2-benzisothiazol-3-amine 1,1-dioxide; and
N-[4-(8-azabicyclo[3.2.1]oct-8-ylsulfonyl)phenyl]-6-[3-(trifluoromethyl)pyridin-2-yl]-1,2-benzisothiazol-3-amine 1,1-dioxide.

8. The compound of claim 3 wherein L is a C$_{1-6}$ alkyl.
9. The compound of claim 8, wherein G is aryl.
10. The compound of claim 9, wherein G is phenyl.
11. The compound of claim 10, wherein the compound is selected from the group consisting of N-(4-tert-butylbenzyl)-6-(3-chloropyridin-2-yl)-1,2-benzisothiazol-3-amine 1,1-dioxide; and N-[2-(4-tert-butylphenyl)ethyl]-6-(3-chloropyridin-2-yl)-1,2-benzisothiazol-3-amine 1,1-dioxide.
12. The compound of claim 2 wherein A is pyrimidinyl.
13. The compound of formula 12, wherein L is a bond.
14. The compound of claim 13, wherein G is aryl.
15. The compound of claim 14, wherein G is phenyl.
16. The compound of claim 15, wherein the compound is selected from the group consisting of N-(4-tert-butylphenyl)-6-pyrimidin-2-yl-1,2-benzisothiazol-3-amine 1,1-dioxide; and 6-pyrimidin-2-yl-N-{4-[(trifluoromethyl)sulfonyl]phenyl}-1,2-benzisothiazol-3-amine 1,1-dioxide.
17. The compound of claim 2 wherein L is C$_{1-6}$ alkyl.
18. The compound of claim 17 wherein G is aryl.
19. A pharmaceutical composition comprising a therapeutically effective amount of a compound of formula (I) as defined in claim 1 or a pharmaceutically acceptable salt thereof.

* * * * *

UNITED STATES PATENT AND TRADEMARK OFFICE
CERTIFICATE OF CORRECTION

PATENT NO. : 7,615,570 B2  
APPLICATION NO. : 11/294316  
DATED : November 10, 2009  
INVENTOR(S) : Brown et al.

Page 1 of 1

It is certified that error appears in the above-identified patent and that said Letters Patent is hereby corrected as shown below:

Column 31, line 6, claim 1: "(O)N(alkyl)$_2$;" to read as --(O)N(alkyl)$_2$,--

Column 31, line 26, claim 7: "[3.2.1]" to read as --[3,2,1]--

Column 32, line 6, claim 7: "[3.2.1]" to read as --[3,2,1]--

Column 32, line 12, claim 7: "[3.2.1]" to read as --[3,2,1]--

Colurnn 32, line 12, claim 7: "fluorophenyl" to read as --fluoromethyl--

Column 32, line 18, claim 7: "[3.2.1]" to read as --[3,2,1]--

Column 32, line 30, claim 13: "formula 12" to read as --claim 12--

Signed and Sealed this  
First Day of March, 2011

David J. Kappos  
*Director of the United States Patent and Trademark Office*